US007288254B2

(12) United States Patent
Neville et al.

(10) Patent No.: US 7,288,254 B2
(45) Date of Patent: Oct. 30, 2007

(54) USE OF IMMUNOTOXINS TO INDUCE IMMUNE TOLERANCE TO PANCREATIC ISLET TRANSPLANTATION

(75) Inventors: David M. Neville, Bethesda, MD (US); Judith T. Thomas, Birmingham, AL (US); Francis T. Thomas, Birmingham, AL (US)

(73) Assignee: The United States of America as represented by the Secretary, Department of Health and Human Services, NIH, Washington, DC (US)

( * ) Notice: Subject to any disclaimer, the term of this patent is extended or adjusted under 35 U.S.C. 154(b) by 0 days.

(21) Appl. No.: 09/810,999

(22) Filed: Mar. 16, 2001

(65) Prior Publication Data

US 2001/0024645 A1 Sep. 27, 2001
US 2005/0142117 A9 Jun. 30, 2005

Related U.S. Application Data

(63) Continuation-in-part of application No. 09/064,413, filed on Apr. 22, 1998, now abandoned, and a continuation-in-part of application No. 09/636,251, filed on Aug. 10, 2000, now abandoned, which is a continuation of application No. 08/843,409, filed on Apr. 15, 1997, now Pat. No. 6,103,235, said application No. 09/636,251 and a continuation of application No. 08/739,703, filed on Oct. 29, 1996, now abandoned, application No. 09/810,999, and a continuation-in-part of application No. 09/368,069, filed on Aug. 3, 1999, now abandoned, is a continuation of application No. 08/878,378, filed on Jun. 18, 1997, which is a continuation of application No. 08/628,745, filed as application No. PCT/US96/05087 on Apr. 12, 1996, now abandoned, said application No. 08/878,378 is a continuation-in-part of application No. 08/739,703, filed on Oct. 29, 1996, now abandoned, said application No. 08/878,378 is a continuation of application No. PCT/US96/05087, filed on Apr. 12, 1996, application No. 09/810,999, and a continuation-in-part of application No. 09/380,484, filed as application No. PCT/US98/04303 on Mar. 5, 1998, now Pat. No. 6,632,928.

(60) Provisional application No. 60/039,987, filed on Mar. 5, 1997, provisional application No. 60/015,459, filed on Apr. 15, 1996, provisional application No. 60/008,104, filed on Oct. 30, 1995.

(51) Int. Cl.
*A61K 39/00* (2006.01)

(52) U.S. Cl. .................. 424/178.1; 424/192.1; 424/93.71; 424/177.1; 514/866; 530/387.3; 530/388.13; 530/389.6; 530/391.7

(58) Field of Classification Search ............ 424/178.1, 424/192.1, 93.71, 177.1; 514/866; 530/387.3, 530/388.13, 389.6, 391.7
See application file for complete search history.

(56) References Cited

U.S. PATENT DOCUMENTS

| 5,167,956 | A | * | 12/1992 | Neville, Jr. et al. | ........ | 424/85.91 |
|---|---|---|---|---|---|---|
| 5,725,857 | A | | 3/1998 | Neville, Jr. | | |
| 5,736,536 | A | | 4/1998 | Siegall et al. | | |
| 6,103,235 | A | | 8/2000 | Neville et al. | | |

FOREIGN PATENT DOCUMENTS

| DE | 4024187 A1 | 7/1990 |
|---|---|---|
| EP | 0 332 174 A | 3/1989 |
| EP | 0306 943 | 3/1989 |
| EP | 0306943 * | 3/1989 |
| EP | 0616034 A | 9/1994 |
| WO | WO8702987 | 5/1987 |
| WO | WO89/06968 | 8/1989 |
| WO | WO9213562 | 8/1992 |
| WO | WO9113157 | 9/1992 |
| WO | WO9315113 | 8/1993 |
| WO | WO8400382 A | 2/1994 |
| WO | WO9533481 | 12/1995 |
| WO | WO9632137 | 10/1996 |
| WO | WO9839363 | 9/1998 |
| WO | WO9839425 | 9/1998 |
| WO | WO99/53954 | 10/1999 |

(Continued)

OTHER PUBLICATIONS

Shalby et al. J. Eyp. Med. 175: 217, 1992.*

(Continued)

*Primary Examiner*—G. R. Ewoldt
(74) *Attorney, Agent, or Firm*—Needle & Rosenberg, P.C.

(57) ABSTRACT

The invention provides a method of treating diabetes in a subject, comprising administering to the diabetic subject an immunotoxin, thereby reducing the subject's T-cell population, and administering to the subject pancreatic islet cells from a donor. The immune tolerance inducing treatment regimen, used optionally with adjunct immunosuppressive agents, prevents pancreatic islet cell rejection while maintaining long term islet cell function following xenogeneic and allogeneic pancreatic islet cell transplantation. Thus, the methods of the present invention provide a means for treating diabetes, wherein the need for exogenous insulin or immunosuppressive agents is decreased or eliminated. Also provided is a method of inhibiting a rejection response of a transplant recipient, comprising administering an immunotoxin during the peritransplant period, thereby transiently reducing the number of T-cell lymphocytes and promoting long-term survival of the transplant.

8 Claims, 7 Drawing Sheets

FOREIGN PATENT DOCUMENTS

| | | |
|---|---|---|
| WO | WO 00/40270 | 7/2000 |
| WO | WO 00/41474 | 7/2000 |
| WO | WO 00/61132 | 10/2000 |

OTHER PUBLICATIONS

Shu et al. PNAS 90: 7995, 1993.*
Parren et al. Res. Immunol. 142: 749, 1991.*
Lu et al (J. Am. Soc. Nephrol., 4:1239-1256, 1993.*
Nemoto et al (Agents Actions, 36:306-311, 1992.*
Koehler et al (Bone Marrow Transplantation, 13:571-575, 1994.*
Gontel et al (1999) J. Natl. Cancer Inst. 81(10):775-781.*
Vitetta et al(1991) Cancer Res. 51(15): 4052-4058.*
Hertler et al (1988) J. Biol. Response. Med. 7: 97-113.*
Greenfield et al (1987) Science 238: 536-539.*
Johnson et al(1988) J.Biol. Chem 263(3):1295-1300.*
Myers et al (1989) J. Immunol. Methods 121 :129-142.*
Neville,Jr et al (1989) J Biol Chem. 264(35):14653-61.*
Urban et al (1988) Cell 54 :577-592.*
Pastan et al (1991) Science 254 : 1173-1177.*
Hauser (1991) Science 254 :1167-1172*
Osband et al (1990) Immunology Today 11(6):193-195.*
Waldmann (1991) Science252: 1657-1662.*
Youle, R.J. et al., "Immunotoxins Show Rapid Entry of Diphtheria Toxin But Not Ricin Via The T3 Antigen," *J. Immunol.* 136(1):93-98 (Jan. 1, 1986).
Chaudhary, V.K. et al., "A Recombinant Single-Chain Immunotoxin Composed of anti-Tac Variable Regions and a Truncated Diphtheria Toxin," *Proc. Natl. Acad. Sci.* USA, 87:9491-9494 (Dec. 1990).
Lenscnow, D.J. et al., "Long-Term Survival of Xenogeneic Pancreatic Islet Grafts Induced by CTLA4lg," *Science* 257:789-792 (Aug. 7, 1992).
Waldmann, H. et al.,"The Use of Monoclonal Antibodies to Achieve Immunological Tolerance," *TIPS* 14:143-148 (May 1993).
Boussiotis, V.A. et al., "Blockade of the CD28 Co-Stimulatory Pathway: a means to induce tolerance," *Curr. Opin. Immunol* .6:797 (1994).
Schwartz, R.H., "Models of T Cell Anergy: Is There a Common Molecular Mechanism?," *J. Exp. Med.* 184:1-8 (Jul. 1996).
Liu, Y.Y. et al., "Expression of an Anti-CD3 single-Chain Immunotoxin with a Truncated Diphtheria Toxin in a Mutant CHO Cell Line," *Protein Expression and Purification* 19:304-311 (2000).
Barber, W.H. et al. *Transplantation* (1991) 51:70-75, January.
Barr et al. *Science* (1991) 254:1507-1509.
Behara et al. *The FASEB Journal* (1992) 6:2853-2858.
Billingham et al. *Nature* (1953) 172:603-606.
Blazar, B.R. et al. *J. Immunol.* (1991) 147:1492-1503, September.
Brent et al. *Nature* (1962) 196:1298-1301.
Caves et al. *Transplantation* (1973) 16:252-256.
Coffin, J.C. *Science* (1992) 255:411-413, January.
Contreas et al. *Transplantation* (1998) 65(9):1159-1169.
DeWet et al. *Moll. Cell. Biol.* (1987) 7:725-737.
Fabre et al. *Transplantation* (1972) 14:608-617.
French et al. *The Lancet* (1969) 1103-1106.
Gould et al. *J. Natl. Cancer Inst..* (1989) 81:775-781, May 22.
Gowland, G. *Brit Med. Bull.* (1965) 21:123-128.
Greenfield et al. *Science* (1987) 238:536-539.
Henretta et al. *Transplantation Proceedings* (1994) 26: 1138-1139.
Hertler et al. *J. Biol. Response Mod.* (1988) 7:97-113.
Hirsch et al. *Transplantation* (1990) 49(6):1117-1123, June.
Hoffman, M. *Science* (1991) 254:1455-1456.
Hu et al. *Cellular Immunology* (1997) 177:26-34.
Hullett et al. *Transplantation Proceedings* (1993) 25(1):756-757.
Izquierdo et al. *Int. J. Cancer* (1989) 43:697-702.
Janeway, C. *Nature* (1991) 349:459-461.
Johnson et al. *J. Neurosurg.* (1989) 70:240.
Johnson et al. *J. Biol. Chem.* (1988) 263(3):1295-1300.
Kamada et al. *Transplantation* (1981) 13:837-841.
Kamada et al. *Immunology Today* (1985) 6:336-342.
Kappler et al. *Science* (1989) 244:811-813, May 19.
Knechtle et al. *Transplantation* (1994) 57:990-996.
Knechtle et al. *Transplantation* (1997) 63:1-6.
Koehler et al. *Bone Marrow Transplantation* (1994) 13:571-575.
Laurence et al. *Nature* (1992) 358:255-259, July.
Little et al. *Transplantation* (1975) 19:53-59.
Lu et al. *J. Am. Soc. Nephrol.* (1993) 4:1239-1256.
Madsen et al. *Nature* (1988) 332:161-164.
Marsh & Neville *Biochem.* (1986) 25(15):4461-4467.
Mellor et al. *Cell* (1984) 36:139-144.
Moller et al. *J. Clin. Invest.* (1988) 82:1183-1191.
Murphy et al. *Science* (1990) 250:1720-1723.
Myers et al. *J. Immunol. Meth.* (1989) 121:129-142.
Nemoto et al. *Agents Action* (1992) 36:306-311.
Neville et al. *Proc. Natl. Acad. Sci.* USA (1992) 89:2585-2589.
Neville & Marsh, Frankel ed. *Immunotoxins* Kluwer Academic Publishers, Chapter 21. methods for quantifying Immunotoxin Efficacy, (1998) 393-404.
Neville et al. *J. Controlled Release* (1993) 24(1-3):133-144, May.
Neville in CRC Crit. Rev. in Therap. Drug Carrier Syst., CRC Press Inc., (1986) 2(4):329-352.
Neville et al. *J. Biol. Chem.* (1989) 264(25):14653-14661.
Neville & Hudson *Ann. Rev. Biochem.* (1986) 55:195-224.
Neville et al. *J. Immunotherapy* (1996) 19(2):85-92.
Nooij et al. *Eur. J. Immunol.* (1986) 16:975-979.
Nooij & Jonker *Eur. J. Immunol.* (1987) 17:1089-1093.
Ohzato et al. *Transplantation Proceedings* (1993) 25:297-298.
Oksenberg et al. *Nature* (1993) 362:68-70, March.
Oluwole et al. *Translantation Immunity and GVH Disease II* Abstract 2723 FASEB (1992).
Oluwole et al. *Transplantation Proceedings* (1993) 25(1):299-300.
Osband et al. *Immunology Today* (1990) 11(6):193-195.
Parlevliet et al. *Transplantation* (1990) 50:889-892, November.
Parren et al. *Res. Immunol.* (1992) 142:749763.
Pastan et al. *Science* (1991) 254:1173-1177, Nov. 22.
Pearson, T.C. et al. *Transplantation* (1992) 54:475-483, September.
Plückthun & Pack *Immunotechnology* (1997) 3:83-105.
Posselt et al. *Science* (1990) 249:1293-1295.
Posselt et al. *Diabetes* (1992) 41:771-775.
Priestley et al. *Transplantation* (1989) 48:1031-1038.
Rada et al. Proc. Natl. Acac. Sci. USA (1990) 87:2167-2171.
Ralston et al. *J. Cell Biol.* (1989) 109:2345-2352.
Remuzzi et al. *Lancet* (1991) 337:750-752.
Ricordi et al. *Transplantation Proceedings* (1997) 29:2240.
Rilo et al. *Transplantation Proceedings* (1995) 27:3162-3163.
Rostaing-Capaillon and Casellas *Cancer Res.* (1990) 50:2909-2916, May 15.
Salmeron et al. *J. of Immunol.* (1991) 147(9):3045-3052, Nov. 1.
Schaffar et al. *Cellular Immun.* (1988) 116:52-59.
Shalaby et al. *J. Exp. Med.* (1992) 175:217-225.
Shapiro et al. *Proc. Soc. Exp. Biol.* (1961) 106:472-475.
Shu et al. *PNAS* (1993) 9:7995-7999.
Stuart et al. *Science* (1968) 160:1463-1465.
Sumimoto et al. *Transplantation* (1990) 50:678-682.
Thomas et al. *Transplantation* (1994) 57:101-115.
Thomas et al. *Transplantation* (1997) 64: 124.
Thomas et al. *Transplantation Proceedings* (1995) 27: 3167.
Thompson et al. *J. Biol. Chem.* (1995) 270(47):28037-28041, Nov. 24.
Thorpe et al. *J. Nat'l Cancer Inst.* (1985) 75(1):151-159, July.
Urban et al. *Cell* (1988) 54:577-592, Aug. 12.
Vitetta et al. *Cancer Res.* (1991) 51:4052-4053, Aug. 1.
Waldmann, T. *Science* (1991) 252:1657-1662.
Waldmann, H. et al. *TiPS* (1993) 14:143-148, May.
Whitlow & Filupa *Methods* (1991) 2 (2):97-105.
Wilson et al., *Transplantation* (1969) 7:360-371.
Wood et al. *Transplantation* (1985) 39:56-62.
Wray et al. *Transplantation* (1992) 52:167-174.
Yamaguchi et al. *Transplant. Proc.* (1989) 21:3555.
Yasumura et al. *Transplantation* (1983) 36:603-609.
Youle & Colombatti *J. Biol. Chem.* (1987) 262:4676-4682 Apr. 5.
Youle & Neville *J. Biol. Chem.* (1982) 257:1598-1601, Feb. 25.
Youle et al. *Cell* (1981) 23:551-558, February.
zur Hausen *Science* (1992) 254:1167-1172, Nov. 22.

Anand et al. *J. Biol. Chem.*, (1991) 266 (32):21874-2879, November.

Hosaka et al. *J. Bio. Chem.* (1991) (19):12127-12130, July.

Jost, Caroline R. et al., J. Biol. Chem. (1994) 269(42):26267-26273, Oct. 21.

Bach, J. "Immunosupressive Therapy of Autoimmune Diseases" *Trends Pharm Sci.* 14(5):213-216 (May 1993).

Vallera, et al. "Anti-CD3 Immunotoxin Prevents Low-Dose STZ/Interferon-Induced Autoimmune Diabetes in Mouse" *Diabetes* 41:457-464 (Apr. 1992).

Herold et al ."Prevention of Autoimmune Diabetes With Nonactivating Anti-CD3 Monoclonal Antibody" *Diabetes* 41(3):385-391 (Mar. 1992).

Traunecker, et al. Bispecific single chain molecules (Janusins) target cytotoxic lymphocytes on HIV infected cells. *The EMBO Journal* (1)12:3655-3659 (1991).

Hayden et al. Single-chain mono- and bispecific antibody derivatives with novel biological properties and antitumor activity from a COS cell transient expression system *Therapeutic Immunology* (1):3-15 (1994).

Ma, et al. Expression and Characterization of a Divalent Chimeric Anti-Human CD3 Single Chain Antibody *Scand. J. Immunol.* 43, 134-139, 1996.

Contreras et al. Tolerability and side effects of anti-CD3-immunotoxin in preclinical testing in kidney and pancreatic islet transplant recipients. *Transplantation* 68(2):215-219 (1999).

Eckhoff et al. ASTS 25$^{th}$ Annual Meeting 1999. Synergy of 15-Deoxyspergualin With Aniti-CD3 Immunotoxin in Tolerance Induction in Rhesus Monkeys. *Transplantation* 67(9):60 (1999).

Faustman, D. Strategies for circumventing transplant rejection: modification of cells, tissues and organs. *Trends in Biotechnology* 13(3):100-105 (1995).

Frankel, A.E. Antibody-toxin hybrids: a clinical review of their use. *J. of Biological Response* 4(5):437-446 (1985).

Haggerty et al. Effect of Deoxyspergualin or CTLA4lg on the Immunogenicity and Pharmacokinetics of the Immunotoxin BR96sFv-PE40 in Dogs. *Journal of Allergy and Clinical Immunology* 99(1):708 (Jan. 1997).

Kieke et al. Isolation of anti-T cell receptor scFv mutants by yeast surface display. *Protein Engineering* 10(11):1303-1310 (1997).

Ma et al. Genetic Construction and Characterization of an Anti-Monkey CD3 Single-Chain Immunotoxin with a Truncated Diphtheria Toxin. *Bioconj. Chem.* 8:695-701 (1997).

Pankewycz et al. Interleukin-2-Diphtheria Toxin Fusion Protein Prolongs Murine Islet Cell Engraftment. *Transplantation* 47(2):318-322 (1989).

Siegall et al. Prevention of immunotoxin-mediated vascular leak syndrome in rats with retention of antitumor activity. *Proc. Natl. Acad. Sci. USA* 91:9514-9518 (1994).

Thomas et al. Reversal of naturally occurring diabetes in primates by unmodified islet xenografts without chronic immunosuppression. *Transplantation* 67(6):846-854 (1999).

Thomas et al. Peritransplant Tolerance Induction in Macaques: Early Events Reflecting the Unique Synergy Between Immunotoxin and Deoxyspergualin. *Transplantation* 68(11):1660-1673 (1999).

Vallera et al. Anti-Graft-Versus-Host Disease Effect of $DT_{390}$-Anti-CD3sFv, a Single-Chain Fv Fusion Immunotoxin Specifically Targeting the CD3ε Moiety of the T-Cell Receptor. *Blood* 88(6):2342-2353 (1996).

Bierhuizen et al. Expression cloning of a cDNA encoding UDP-GlcNAc:Galβ1-3-GalN Ac-R (GlcNAc to GalNac) β1-6GlcNAc transferase by gene transfer into CHO cells expressing polyoma large tumor antigen. *Proc. Natl. Acad. Sci. USA* 89:9326-9330 (1992).

Sreekrishna, Koti "Strategies for Optimizing Protein Expression and Secretion in the Methylotrophic Yeast *Pichia pastoris*," *Industrial Microorganisms: Basic and Applied Molecular Genetics* 16:119-126 (1993).

Woo et al. "Gene optimization is necessary to express a bivalent anti-human anti-T cell immunotoxin in *Pichia pastoris*," *Protein Expression and Purification* 25:270-282 (2002).

\* cited by examiner

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 1
gacatccaga tgacccagac c                                         21

<210> SEQ ID NO 2
<211> LENGTH: 58
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 2
cctcccgagc caccgcctcc gctgcctccg cctccttta tctccagctt gtgtcgcc    58

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 3
gcagcggagg cggtggctcg ggaggggag gctcggaggt gcagcttcag cagtct       56

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 4
gcaagcttga agactgtgag agtggtgcct tg                              32

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 5
gtctcttcaa agcttattgc ctgagctgcc tcccaaa                         37

<210> SEQ ID NO 6
<211> LENGTH: 32
<212> TYPE: DNA
<213> ORGANISM: Artificial Sequence
<220> FEATURE:
<223> OTHER INFORMATION: Description of Artificial Sequence:/note = synthetic construct

<400> SEQUENCE: 6

-continued

```
gcatctagat cagtagcagg tgccagctgt gt                                    32

<210> SEQ ID NO 7
<211> LENGTH: 59
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 7
cggtcgacac catggagaca gacacactcc tgttatgggt actgctgctc tgggttcca       59

<210> SEQ ID NO 8
<211> LENGTH: 51
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 8
gtactgctgc tctgggttcc aggttccact ggggacatcc agatgaccca g               51

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 9
atgaaatacc tattgcctac ggcagccgct ggattgttat tactgcgctg cccaaccagc      60

<210> SEQ ID NO 10
<211> LENGTH: 54
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 10
atgaaatacc tattgcctac ggcagccgct ggattgttat tactcgctgc ccaa            54

<210> SEQ ID NO 11
<211> LENGTH: 59
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 11
ggattgttat tactcgctgc ccaacaagcg atggccggcg ctgatgatgt tgttgattc       59

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 12
```

-continued

```
<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 13
cggtactata aaactctttc caatcatcgt c                                      31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:/note =
      synthetic construct

<400> SEQUENCE: 13
gacgatgatt ggaaagagtt ttatagtacc g                                      31

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence:/note =
      synthetic construct
<223> OTHER INFORMATION: M is A or C

<400> SEQUENCE: 14
agatctgtcg mtcatcagct tttgatttca aaaaatagcg                             40
```

USE OF IMMUNOTOXINS TO INDUCE IMMUNE TOLERANCE TO PANCREATIC ISLET TRANSPLANTATION

This application is a continuation of, and claims the benefit of, U.S. Ser. No. 09/064,413, filed Apr. 22, 1998, now abandoned, herein incorporated in its entirety by reference.

This application is also a continuation in part of U.S. application Ser. No. 09/636,251, filed Aug. 8, 2000, now abandoned, which is a continuation of and claims priority to U.S. application Ser. No. 08/843,409, filed Apr. 15, 1997, now U.S. Pat. No. 6,103,235, which claims benefit of U.S. Provisional Application No. 60/015,459, filed Apr. 15, 1996, and is a continuation of and claims priority to U.S. application Ser. No. 08/739,703, filed Oct. 29, 1996, now abandoned, which claims benefit of U.S. Provisional Application No. 60/008,104, filed Oct. 30, 1995.

This application is also a continuation in part of, and claims priority to, U.S. Ser. No. 09/368,069, filed Aug. 3, 1999 now abandoned, which is a continuation of and claims priority to U.S. Ser. No. 08/878,378, filed Jun. 18, 1997, now abandoned. U.S. Ser. No. 08/878,378 is a continuation of and claims priority to U.S. application Ser. No. 08/628,745 filed Nov. 18, 1996, now abandoned, which is a national stage application of PCT/US96/05087, filed Apr. 12, 1996. U.S. Ser. No. 08/878,378 is also a continuation in part of and claims priority to U.S. application Ser. No. 08/739,703, filed Oct. 29, 1996, now abandoned, which claims the benefit of U.S. Ser. No. 60/008,104, filed Oct. 30, 1995. U.S. Ser. No. 08/878,378 is also a continuation of and claims priority to PCT/US96/05087, filed Apr. 12, 1996.

This application is also a continuation in part of, and claims priority to, U.S. Ser. No. 09/3 80,484 filed Dec. 6, 1999 which claims priority to, international application PCT/US98/04303, filed Mar. 5, 1998, which claims the benefit of U.S. Ser. No. 60/039,987, filed Mar. 5, 1997.

BACKGROUND OF THE INVENTION

1. Field of The Invention

This invention generally relates to techniques for inducing immune tolerance using an immunotoxin. In particular, this invention relates to the use of immune tolerance inducing techniques with pancreatic islet transplantation, for the purpose of inhibiting rejection of the transplant. This invention further relates to the treatment of diabetes using immune tolerance inducing techniques in conjunction with pancreatic islet transplantation.

2. Background Art

There are 16 million diabetics within the United States. Ninety percent of these have Type II diabetes, which is defined by hyperglycemia in the face of normal or elevated levels of circulating insulin. As Type II diabetes progresses, however, a decrease in circulating level of insulin may occur as the beta cells of the pancreatic islets produce and secrete less insulin. The mechanism of insulin resistance in Type II diabetes has not been elucidated, and the condition has proved to be difficult to treat and is currently the leading cause of renal failure in this country.

Type I diabetes results from pancreatic islet beta cell destruction and loss of insulin secretion secondary to an autoimmune process. Type I diabetes generally can be controlled by close monitoring of blood glucose concentration and multiple daily injections of exogenous insulin. Nonetheless, even with insulin replacement therapy, euglycemia is not achieved and at least one half of the Type I population cannot achieve sufficient control to prevent the complications of retinopathy, vasculopathy, and renal deterioration (71,72).

Allografts of pancreatic islets from cadaveric donors have been considered to offer a potential cure for Type I diabetes. Although reversal of type II diabetes by an islet xenograft transplant was described in one study in rodents (74), the conventional wisdom has been that this treatment would only work when insulin secretion was subnormal. In fact clinical tests of islet transplantation have been limited largely to type I diabetics and patients who have previously undergone total pancreatectomy (75).

Even treatment of Type I diabetes with pancreatic islet allografts, however, has not been effective in freeing most patients from exogenous insulin injections (71,73). The problem has been that the immunosuppressive reagents required to inhibit allograft rejection can severely compromise transplanted islet cell function (71). This is unlike the case of renal transplantation where cyclosporine A and corticosteroid derivatives do not severely compromise kidney function, in the majority of cases.

Transplant tolerance remains an elusive goal for patients and physicians whose ideal would be to see a successful, xenogeneic pancreatic islet transplant performed without the need for indefinite, non-specific maintenance immunosuppressive drugs and their attendant side effects. As with many transplant procedures, securing viable allogeneic grafts can be difficult. In addition, long term immunosuppression can be problematic.

Over the past 10 years the majority of transplant recipients have been treated with cyclosporin, azathioprine, and prednisone with a variety of other immunosuppressive agents being used as well for either induction or maintenance immunosuppression. The average annual cost of maintenance immunosuppressive therapy in the United States is approximately $10,000. In addition to the cost, these agents, because of their non-specific effects, have considerable side effects, including compromising islet cell function and increasing susceptibility to infection. A major goal in pancreatic islet transplant immunobiology is the development of specific immunologic tolerance to pancreatic transplants with the potential of freeing patients from the side effects of continuous pharmacologic immunosuppression and its attendant complications and costs.

Anti-T cell therapy (anti-lymphocyte globulin) has been used in rodents in conjunction with thymic injection of donor cells (Posselt et al. *Science* 1990; 249: 1293–1295 and Remuzzi et al. *Lancet* 1991; 337: 750–752). Thymic tolerance has proved successful in rodent models and involves the exposure of the recipient thymus gland to donor alloantigen prior to an organ allograft from the same donor. However, thymic tolerance has never been reported in large animals, and its relevance to tolerance in humans in unknown.

One approach to try to achieve such immunosuppression has been to expose the recipient to cells from the donor prior to the transplant, with the hope of inducing tolerance to a later transplant. This approach has involved placement of donor cells (e.g. bone marrow) presenting MHC Class I antigens in the recipient's thymus shortly after application of anti-lymphocyte serum (ALS) or radiation. However, this approach has proved difficult to adapt to live primates (e.g. monkeys; humans). ALS and/or radiation render the host susceptible to disease or side-effects and/or are insufficiently effective.

If a reliable, safe approach to specific immunologic tolerance to pancreatic islet transplantation, particularly xenogeneic transplantation, could be induced, this would be of tremendous value and appeal to patients and transplant physicians throughout the world with immediate application to new transplants and with potential application to existing transplants in recipients with stable transplant function. Thus, a highly specific immune tolerance inducement is desired. Furthermore, there is a need for a means for imparting tolerance in primates, without the adverse effects of using ALS or radiation. Moreover, the goal is to achieve more than simply delaying the rejection response. Rather, an important goal is to inhibit the rejection response to the point that rejection is not a factor in reducing average life span among transplant recipients.

The present invention meets these needs by providing a method of inducing immune tolerance to pancreatic islet transplantation.

SUMMARY OF THE INVENTION

The invention provides a method of treating diabetes in a subject, comprising administering to the diabetic subject an immunotoxin, thereby reducing the subject's T-cell population, and administering to the subject pancreatic islet cells from a donor. The method is effective for treating Type I or Type II diabetes. More specifically, the invention provides a short course immune tolerance inducing treatment regimen utilizing an anti-CD3 immunotoxin that, optionally with adjunct immunosuppressive agents, prevents pancreatic islet cell rejection while maintaining long term islet cell function following pancreatic islet cell transplantation. The invention further provides sufficient immune tolerance to pancreatic islet transplantation so that xenogeneic transplants are not rejected. Thus, the methods of the present invention provide a means for treating diabetes, wherein the need for exogenous insulin or immunosuppressive agents is eliminated.

A method of inducing immune tolerance using an immunotoxin for xenogeneic or allogeneic pancreatic islet cell transplantation is provided. Also provided is a method of inhibiting a rejection response of a transplant recipient, comprising administering an immunotoxin during the peri-transplant period, thereby transiently reducing the number of T-cell lymphocytes and promoting long-term survival of the transplant.

DETAILED DESCRIPTION OF THE INVENTION

Figure 1:
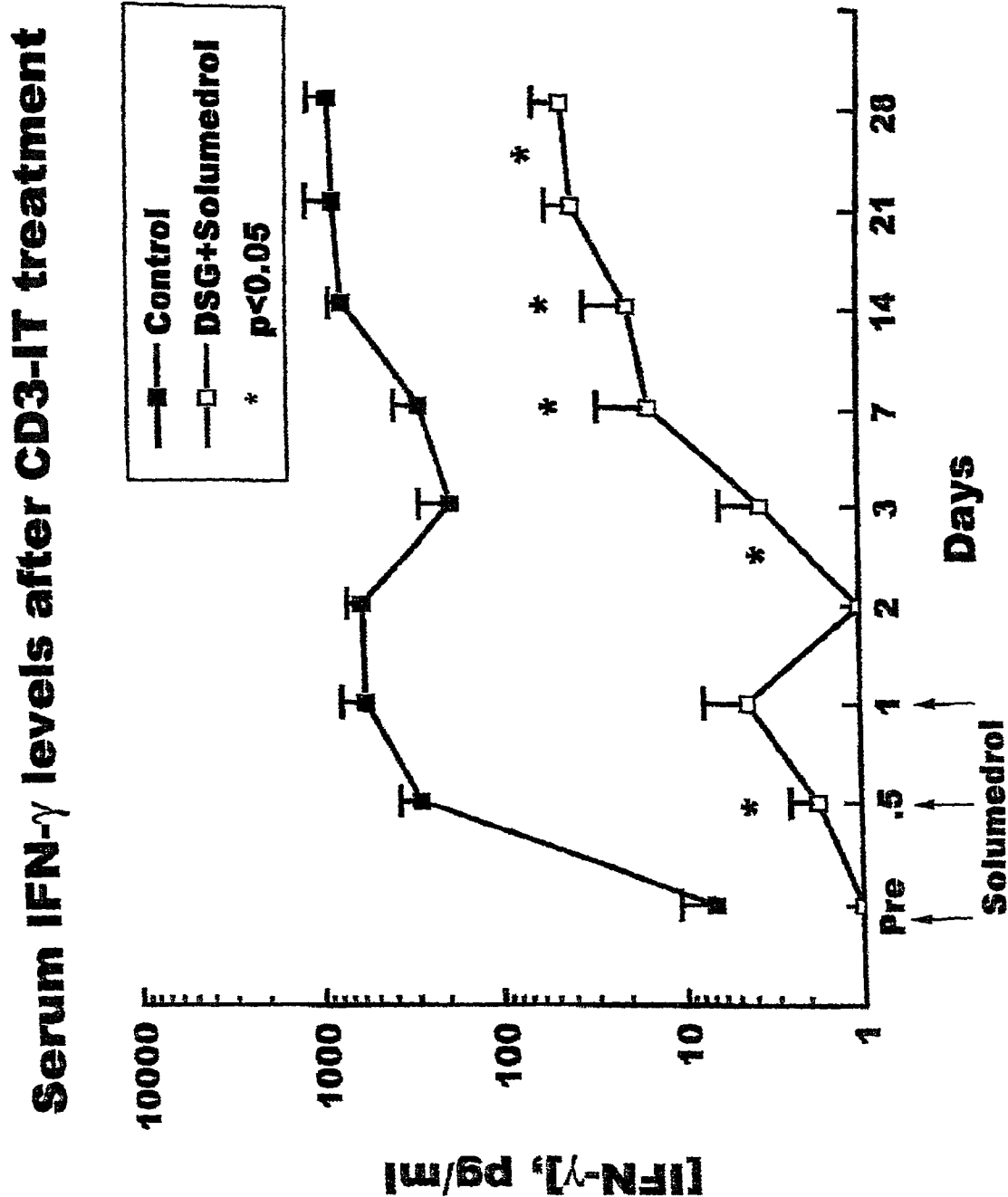
FIG. 1 shows the rise in serum IFN-gamma following FN18-CRM9 immunotoxin treatment in post kidney transplant monkeys with and without treatment with DSG and solumedrol. The treatment dramatically attenuates the rise of IFN-gamma.

The current invention provides a short course immune tolerance inducing treatment regimen utilizing an anti-CD3 immunotoxin that, optionally with adjunct immunosuppressive agents, prevents pancreatic islet cell rejection while maintaining long term islet cell function. A unique feature of the present immunotoxin immune tolerance induction is that the ratio of target cell toxicity (T cell) to non-target cell toxicity (islet cell) is extremely high. The adjunct immunosuppressive agents, which can also be used and which can cause islet cell toxicity, such as cyclosporine and corticosteroid derivatives, are required only for a brief duration due to the power of the primary immunotoxin promoting immune tolerance.

The invention provides a method of treating diabetes in a subject, comprising administering to the diabetic subject an immunotoxin, thereby reducing the subject's T-cell population, and administering to the subject pancreatic islet cells from a donor. Specifically, the method is effective for treating Type I or Type II diabetes. By "diabetes" is meant diabetes mellitus, a metabolic disease characterized by a deficiency or absence of insulin secretion or responsivity of peripheral tissues to insulin. As used throughout, "diabetes" includes Type I, Type II, Type III, and Type IV diabetes mellitus unless specified otherwise.

Unexpectedly, the immune tolerance induction regimen of the invention successfully reverses type II diabetes in monkeys. The reversal of the insulin resistant state in non-human primates suffering from type II diabetes implies that the peripheral insulin resistance seen in this disease is, in some way, mediated by faulty islet function, and this condition can be largely reversed by healthy grafted islets. The present invention can reduce or eliminate the need for insulin replacement in the subject with Type I diabetes as well. In the case of both Type I and Type II, non-fasting blood glucose levels will preferably be maintained below 160 mg/dl upon completion of the immune tolerance induction regimen.

By "pancreatic islet cells" is meant a composition comprising pancreatic islet cells. Preferably the pancreatic islet cells can be transplanted by injection of the cells into the portal vein; however, other cell, tissue, and organ transplantation paradigms well known in the art can be used. It is comtemplated that the immunotherapeutic function of the present immunotolerance tolerance induction regimen can be applied to transplantation of all or part of the pancreas as well as to the transplantation of pancreatic islet cells.

The "donor" can be a cadaver or a living donor. Furthermore, the donor can be of the same species as the subject being treated or a different species than the subject being treated. Thus, using the method of the invention, transplantation can be performed across primate species (i.e., xenogeneic transplantation or xenograft) and within the same primate line (i.e., allogeneic transplantation or allograft). It was not obvious until this invention that the highly sensitive pancreatic islet xenografts would maintain function in the presence of this immune tolerance inducing regimen. Nor was it obvious that this regimen would permit an islet transplantation crossing species lines.

The invention further provides an immune tolerance inducing regimen, wherein a population of the pancreatic islet cells to be transplanted are modified to decrease antigenicity prior to transplantation. Specifically, the donor cells can be altered, such as by genetically engineering the donor or donor cells, to reduce pancreatic islet cell antigenicity or to reduce the susceptibility of pancreatic islet cells to immune injury (R. Weiss, Nature 391: 327–28 (1998)).

The "subject" being treated can include individual humans, domesticated animals, livestock (e.g., cattle, horses, pigs, etc.), and pets (e.g., cats and dogs).

The invention further provides a method, wherein the immunotoxin transiently reduces the subject's T cells in the blood and lymph nodes by at least one log unit. Preferably the number of T cells in the blood and lymph nodes will be transiently decreased by 0.7, 0.8, 0.9, 1, 1.1, 1.2, 1.3, 1.4, 1.5, 1.6, 1.7, 1.8, 1.9, 2 log units, or any interval amount between 0.7 and 2 log units.

By "transiently reduces" is meant that T cells are reduced by 0.7 to 2 log units in the blood and lymph compartments for at least four days before starting to return to normal levels.

The present method of inducing immune tolerance or treating diabetes further comprises administering an immunosuppressive agent to the subject. The immunosuppressive agents can be administered beginning 24 to 0 hours prior to administration of the pancreatic islet cells to the recipient and continuing up to two weeks thereafter. Preferably, the immunosuppressive agents can be administered for at least 4, 5, 6, 7, 8, 9, 10, 11, 12, 13, 14 days, or any interval time. The immunosuppressive agent is selected from the group consisting of cyclosporine, mycophenolate moefitil, methyl prednisolone, deoxyspergualin, other known immunosuppressive agents, and any combination thereof The immunotoxin regimen allows short-term immunosuppressive therapy and eliminates the need for long-term treatment with immunosuppressives, thereby avoiding the side effects associated with chronic immunosuppression.

The immunotoxin is administered beginning at 24 to 0 hours before administration of the pancreatic islet cells and continuing up to several days thereafter. Preferably, the immunotoxin is administered for 1, 2, or 3 days or any time in between. It is contemplated that immunotoxin administration of 4, 5, 6, or 7 days can be used if the production of antitoxin antibodies, which begins after approximately 5 days of administration, can be addressed. The immunotoxin can be administered in subjects beginning anytime after administration of the pancreatic islet cells. Thus, it is contemplated that a subject with a long term surviving transplant, who have not previously received immunotoxin treatment, could still benefit from immunotoxin administration, thereby avoiding the need for long-term treatment with immunosuppressives. It is further contemplated that a transplant recipient who begins to show signs of rejection may benefit from immunotoxin administration to reduce or eliminate the rejection process.

The invention further provides a method of inhibiting a rejection response of a recipient of a pancreatic islet transplant by inducing immune tolerance in the recipient, comprising administering an immunotoxin during the peritransplant period, thereby transiently reducing the number of T-cell lymphocytes and promoting long-term survival of the transplant. By "peritransplant period" is meant the period between 24 hours prior to and 2 weeks after transplantation.

Because of the close similarities between the immune functions that govern graft acceptance and rejection within primates and the similar functions of the pancreata within primates, this tolerance induction regimen is considered likely to succeed in humans for the treatment of diabetes via islet transplantation.

The immunotoxin can be a divalent anti-T cell immunotoxin, such as UCHT1-CRM9. More specifically, the divalent anti-T cell immunotoxin can be a single chain engineered fusion protein comprising an amino-terminus DT based toxin domain fused to a sFv domain (VL-linker-VH where linker is (Gly4Ser)3 separated by a second linker and fused to a second identical sFv domain. The second linker can be (Gly4Ser)3 or (Gly4Ser)5. Alternatively, the single chain engineered fusion protein can be monovalent providing that the linker and the VL and VH sequence are carefully chosen to provide an affinity lying within ±0.5 log unit of the parental antibody affinity.

The divalent disulfide linked immunotoxin can have identical components. Alternatively, the components can be non-identical with only one toxin moiety to minimize stearic hindrance of the antigen binding domains. The divalent anti-T cell immunotoxin can be a disulfide dimer of two monovalent single chain engineered fusion proteins that are dimerized via the hinge region of IgG1 or the μCH2 domain of IgM. The dimer can be a homo dimer comprising two monovalent units of DT390-sFv-H-γ CH3, disulfide dimerized by the single or double cysteine residues in H the hinge region. The dimer alternatively can be a heterodimer comprising one monovalent unit of DT390-sFv-H-γCH3, disulfide dimerized by the single or double cysteine residues in H to a monovalent unit of sFv-H-γCH3. Dimerization can be achieved in vivo by expression in a eukaryotic expression system modified for toxin resistance by an EF2 mutation. Examples are mutated CHO cells, Ss9 insect cells, or mutated yeasts. Alternatively, dimerization can be performed in vitro from monovalent species produced in prokaryote expression systems by the use of disulfide interchange reactions employing suitable disulfide oxidation systems such as dithiobisnitrobenzoic acid used to generate mixed disulfide intermediates.

The divalent anti-T cell immunotoxin can comprise a toxin moiety and a targeting moiety directed to the T cell CD3∈ epitope. Even more specifically, the toxin moiety can be a diphtheria toxin binding site mutant. The immunotoxin can comprise a mutant toxin moiety (e.g., DT toxin or ETA toxin) linked to a single chain (sc) variable region antibody moiety (targeting moiety). Thus, the invention utilizes an immunotoxin having recombinantly produced antibody moiety linked (coupled) to a recombinantly produced toxin moiety and a fusion immunotoxin (where both toxin and antibody domains are produced from a recombinant construct). As the application provides the necessary information regarding the arrangement of toxin and antibody domains, and the sub regions within them, it will be recognized that any number or chemical coupling or recombinant DNA methods can be used to generate an immunotoxin. Thus, reference to a fusion toxin or a coupled toxin is not necessarily limiting.

The antibody moiety preferably routes by the anti-CD3 pathway. The immunotoxin can be monovalent, but divalent antibody moieties are presently preferred since they have been found to enhance cell killing by about 3 to 15 fold. The immunotoxin can be a fusion protein produced recombinantly. The immunotoxin can be made by chemical thioether linkage at unique sites of a recombinantly produced divalent antibody (targeting moiety) and a recombinantly produced mutant toxin moiety. The targeting moiety of the immunotoxin can comprise the human μCH2, γCH3 and μCH4 regions and VL and VH regions from murine Ig antibodies. These regions can be from the antibody UCHT1 so that the antibody moiety is scUCHT1, which is a single chain CD3∈ antibody having human μCH2, γCH3 and μCH4 regions and mouse variable regions. These are believed to be the first instances of sc anti-CD3 antibodies. Numerous DT mutant toxin moieties are described herein, for example DT390 or extensions of DT390 out to DT530. Thus, as just one specific example the immunotoxin, the invention provides scUCHT1-DT390. Derivatives of this immunotoxin are designed and constructed as described herein.

The engineered divalent immunotoxin utilized in the present invention can be stabilized with respect to divalency and disulfide bond initiation by the interactive Ig domains of either human IgM μCH2 or IgGI γCH3 or other similar Ig interactive domains.

In the present invention, the toxin moiety retains its toxic function and membrane translocation function to the cytosol in full amounts. The loss in binding function located in the receptor binding domain of the toxin protein diminishes systemic toxicity by reducing binding to non-target cells. Thus, the immunotoxin can be safely administered. The routing function normally supplied by the toxin binding function is supplied by the targeting antibody, for example, anti-CD3. The essential routing pathway is (1) localization to coated pits for endocytosis, (2) escape from lysosomal routing, and (3) return to the plasma membrane.

The mutant DT toxin moiety can be a truncated mutant, such as DT390, extensions of DT390 out to DT530, or other truncated mutants, as well as a full length toxin with point mutations or CRM9 (cloned in C. ulcerans), scUCHT1 fusion proteins with DTM1 and DT483. DT390 has been cloned and expressed in E. coli. The toxin domain can be CRM9 (DT535, S525F) plus a second attenuating mutation from the group: F530A, K516E, K516A, Y514A, V523A, N524A). The antibody moiety can be scUCHT1 or other anti-CD3 antibody having the routing and other characteristics described in detail herein. Thus, one example of an immunotoxin for use in the present methods is the fusion-protein immunotoxin DT390sSvUCHT1. In principal, described immunotoxins can be used in the methods of the invention.

The immunotoxin or components thereof can be expressed in E. coli BL21DE3 cytosol using TrxB⁻strains at 15 to 25° C. Alternatively, the immunotoxin or components thereof can be expressed in eukaryotic cell lines (such as CHO), insect cell lines (such as Ss9), and yeast cell lines (such as Pichia pastoris) provided that the toxin glycosylation sites at residues 16 and 235 are eliminated and the cells have been mutated to resist ADP-ribosylation catalyzed by toxin, by a Gly to Arg substitution 2 residues to the carboxyl side of the modified amino acid diphthamide. In the case of insect cells this mutant EF-2 can be supplied in the same baculovirus vector supplying the immunotoxin gene since two late promoters are available in baculovirus.

The recombinant immunotoxins can be produced from recombinant sc divalent antibody or recombinant dicystronic divalent antibody and recombinant mutant toxins each containing a single unpaired cysteine residue. An advantage of this method is that the toxins are easily produced and properly folded by their native bacteria while the antibodies are better produced and folded in eukaryote cells. In addition, this addresses differences in coding preferences between eukaryotes and prokaryotes which can be troublesome with some immunotoxin fusion proteins.

The general principles for producing the present divalent recombinant anti-T cell immunotoxins are:

1. The disulfide bond bridging the two monovalent chains is chosen from a natural Ig domain, for example from μCH2 (C337 of residues 228–340 or the γIgG hinge region, C226 or C229 or both of residues 216–238 [with C220P]).

2. Sufficient non-covalent interaction between the monovalent chains is supplied by including domains having high affinity interactions and close crystallographic or solution contacts, such as μCH2, μCH4 (residues 447–576) or γCH3 (residues 376–446). These non-covalent interactions facilitate proper folding for formation of the interchain disulfide bond.

3. For fusion immunotoxins the orientation of the antibody to the toxin is chosen so that the catalytic domain of the toxin moiety becomes a free entity when it undergoes proteolysis at its natural processing site under reducing conditions. Thus, in the ETA based IT, the toxin moiety is at the carboxy terminus and, in DT based fusion IT, the DT based toxin moiety is at the amino terminus of the fusion protein.

4. For chemically coupled immunotoxins, a single cysteine is inserted within the toxin binding domain. The antibody is engineered to have only a single free cysteine per chain which projects into the solvent away from interchain contacts such as μCH3 414, μCH4 575 or the addition to γCH3 at C447. Crystal structure indicates this region is highly solvent accessible. Excess free cysteines are converted to alanine. Alternatively, a C terminal cysteine can be added to γCH3 directly following a histidine tag for purification, γCH3 (His)6Cys.

5. Toxins are mutated in their binding domain by point mutations, insertions or deletions, have at least a 1000 fold reduction in binding activity over wild type, and are free of translocation defects.

6. Toxin binding site mutants, if not capable of proteolytic processing at neutral pH, are modified in the processing region to achieve this result.

A binding site mutant (CRM9) of full length diphtheria toxin residues 1–535 using the numbering system described by Kaczovek et al. (56) S525F (57) can be further modified for chemical coupling by changing a residue in the binding domain (residues 379–535) to cysteine. Presently preferred residues are those with exposed solvent areas greater than 38%. These residues are K516, V518, D519, H520, T521, V523, K526, F530, E532, K534 and S535 (57). Of these K516 and F530 are presently preferred since they are likely to block any residual binding activity (57). However, maximal coupling of the new cysteine residue will be enhanced by the highest exposed solvent surface and proximity to a positively charged residue (which has the effect of lowering cysteine—SH pKa). These residues are at D519 and S535 so that these are presently preferred from the above list of possibilities.

A double mutant of DT containing the S525F mutation of CRM9 plus an additional replacement within the 514–525 exposed binding site loop to introduce a cysteine coupling site for example T521C can be produced in Corynebacterium ulcerans preceded by the CRM9 promoter and signal sequence. The double mutant is made in Corynebacterium ulcerans by a recombination event between the plasmid producing CRM9-antibody fusion protein and PCR generated mutant DNA with a stop codon at 526 (gapped plasmid mutagenesis). Alternatively, double attenuating mutants of diphtheria toxin can be produced in E. coli BL21DE3 TrxB⁻ by PCR mutagenesis without the use of a signal sequence. These CRM9-Cs can be used to form specific thioether mutant toxin divalent antibody constructs by adding excess bismaleimidohexane to CRM9-Cs and coupling to single chain divalent antibody containing a free cysteine at either the end of the μCH4 domain or the γCH3 domain (see Ser. No. 08/739,703, hereby incorporated by reference).

These and other mutations are accomplished by gapped plasmid PCR mutagenesis (58) using the newly designed *E. coli*/*C. ulcerans* shuttle vector yCE96 containing either the double mutant DT S508F S525F or a CRM9 COOH terminus fusion protein construct having reduced toxicity due to the COOH terminal added protein domain (59).

The mutated toxins are produced and purified analogously to the parent toxin except that low levels of reducing agent (equivalent to 2 mM betamercaptoethanol) are included in the purification to protect the unpaired introduced —SH group. Thioether chemical coupling is achieved to a single unpaired cysteine within the divalent antibody construct at either residue 414 in domain γCH-3 or residue 575 in domain μCH4 when this domain is included. In this case domain γCH-3 is mutated C414A to provide only a single coupling site. An advantage of including μCH4 is enhanced stability of the divalent antibody. A disadvantage is that the extra domain increases size and thereby reduces the secretion efficiency during antibody production. The advantage of terminating with the γCH3 domain is that, in another variant, a His6 purification tag can be added at either the μCH2 COOH or γCH3 COOH terminus to facilitate antibody purification. Another variant is to use the γ hinge region to form the interchain disulfide and to couple through a γCH3 or μCH4. This variant has the advantage of being smaller in size and places the toxin moiety closer to the CD3 epitope binding domains, which could increase toxin membrane translocation efficiency. A His tag can be included at the carboxy terminus as a purification aid. SH-CRM9 is concentrated to 10 mg/ml in PBS pH 8.5 and reacted with a 15 fold molar excess of bismaleimidohexane (BW (Pierce, Rockford, Ill.). Excess BMH is removed by passing over a small G25F column (Pharmacia, Piscataway, N.J.). The maleimide derived toxin at about 5 mg/ml is now added to scUCHT1 divalent antibody at 10 mg/ml at room temperature. After 1 hr the conjugate is separated from non-reactive starting products by size exclusion HPLC on a 2 inch by 10 inch MODcol column packed with Zorbax (DuPont) GF250 6 micron resin (for large scale production). Derivatives of ETA60EF61cys161 are also coupled to scUCHT1 divalent antibody by the same method.

Divalent anti-T cell fusion immunotoxins based on DT can be utilized in the invention, wherein the toxin domain (also referred to herein as "toxin moiety" or "tox") is either full length mutant S525F (CRM9) or truncated at 390 or 486 (collectively Tox) and the sequence of domains from the amino terminus from left to right can be selected from among the following and may include C terminal or amino terminal His purification tags: VL and VH are the variable light and heavy domains of the anti-CD3 antibody UCHT1 or other anti-CD3 antibody. H is the human IgG1 hinge.

Single chain divalent fusion protein: Tox, VL, L, VH, L, VL, L, VH;

Single chain univalent fusion protein homodimerized via μCH2 337 Cys: (Tox, VL, L, VH, μCH2)2;

Single chain univalent fusion protein homodimerized via H 226/229 Cys: (Tox, VL, L, VH, H, γCH3)2;

Single chain univalent fusion protein heterodimerized via μCH2 337 Cys: (Tox, VL, L, VH, μCH2 VL, L, VH, μCH2);

Single chain univalent fusion protein heterodimerized via H 226/229 Cys: (Tox, VL, L, VH, H, γCH3 VL, L, VH, H, γCH3);

sFv-SH fusion protein homodimerized via H 226/229 Cys chemically linked via a bis maleimide (R) to a SH derivatized CRM9 or a CRM9 containing an engineered C terminal cysteine (Tox): VL, L, VH, H, γCH3, His6, Cys-SH-R-SH-Tox.

Other types of protein toxin moieties can be utilized in anti-T cell immunotoxins for the induction of tolerance. All that is required is that a 1-2 log kill of T cells within the blood and lymph node compartments can be achieved without undue systemic toxicity. This in turn requires that the routing epitope routes in parallel with the toxin intoxication pathway and that binding site mutants are available or that toxins truncated in their binding domain are available that reduce toxin binding by 1000 fold compared to wild type toxins without compromising toxin translocation efficiency (see U.S. Pat. No. 5,167,956 issued Dec. 1, 1992). In addition when using targeting via antibodies, divalent antibodies are generally required under in vivo conditions to achieve sufficient cell killing due to the 3 to 15 fold lower affinity of monovalent antibodies. However, the method of linking the toxin to the divalent antibody either as a single chain fusion protein or through specific engineered coupling sites must not interfere with translocation efficiency. This could occur due to the larger size of many divalent antibodies compared to monovalent scFv antibodies unless care is taken so that the catalytic domain of the toxin can achieve unencumbered translocation. This is achieved for DT based immunotoxins using DT based binding site mutants where the fusion protein antibody moiety is contiguous with the COOH terminus of the toxin binding chain as described above. This allows the catalytic a chain to translocate as soon as the disulfide loop spanning the Arg/Ser proteolytic processing site residues 193/194 is reduced. Most targeted cells are capable of performing this processing event, and when chemically coupled CRM9 is used the processing is performed by trypsin prior to coupling.

If the toxin moiety is based on full length diphtheria toxin, it can include the following mutations:

S525F, K530C
S525F, K516C
S525F, D519C
S525F, S535C.

The antibody-toxin constructs utilized in the invention can be expected to be effective as immunotoxins because the relevant parameters are known. The following discussion of parameters is relevant to the use of the immunotoxin in tolerance induction. The relevant binding constants, number of receptors and translocation rates for humans have been determined and used. Binding values for anti-CD3-CRM9 for targeted and non-targeted cells in vitro and rates of translocation for the anti-CD3-CRM9 conjugate to targeted and non-targeted cells in vitro are described (Greenfield et is al. (1987) *Science* 238:536; Johnson et al. (1988) *J. Biol. Chem.* 263:1295; Johnson et al. (1989) *J. Neurosurg.* 70:240; and Neville et al. (1989) *J. Biol. Chem.* 264:14653). The rate limiting translocation rate to targeted cells in vitro is shown as follows: an anti-CD3 -CRM9 conjugate at $10^{-11}$ M is translocated to about 75% of the target cells present as measured by inhibition of protein synthesis in about 75% of cells with 20 hours. Inhibition of protein synthesis is complete in cells into which the conjugate translocates.

Parameters determined in in vivo studies in nude mice include the following: Tumor burden is described in Example 1 as a constant mass equal to 0.1% of body weight; the receptor number and variation of receptor number are described in Example 3; "favorable therapeutic margin" is defined as an in vivo target cell 3 log kill at 0.5 MLD (minimum lethal dose)-comparison of efficacy with an established treatment of 0.5 MLD immunotoxin equivalent (group 1) to a radiation dose of 500–600 cGy (groups 8 and 9).

The parameters determined in vitro allowed the prediction of success in the in vivo nude mouse study. The prediction of in vivo success was verified by the data in Examples 3–4. Using the target cell number from the mouse study as being equivalent to the local T cell burden in a monkey or man successful T cell ablation and immunosuppression in monkeys could be predicted. This prediction has been verified by the monkey data in Example 5. Using the same parameters, a scientist skilled in this field can make a prediction of success in humans with confidence, because these parameters have been previously shown to have predictive success.

Most human sera contain anti-DT neutralizing antibodies from childhood immunization. To compensate for this the therapeutic dose of anti-CD3-CRM9 can be appropriately raised without affecting the therapeutic margin. Alternatively, a non-toxic DT mutants reactive with neutralizing antisera (e.g., CRM197) that can be administered in conjunction with the immunotoxin. See U.S. Pat. No. 5,725,857, the content of which is incorporated herein by reference.

One embodiment to the invention provides a method of inhibiting a rejection response by inducing immune tolerance in a recipient to a foreign donor pancreatic islet cell by exposing the recipient to an immunotoxin so as to reduce the recipients's peripheral blood T-cell lymphocyte population by at least 80%, and preferably 95% or higher, wherein the immunotoxin is an anti-CD3 antibody linked to a diphtheria protein toxin, and wherein the protein has a binding site mutation. The term "donor cell" refers to a donor pancreatic islet cell or cells, as distinguished from donor lymphocytes or donor bone marrow. When the donor pancreatic islet cells are transplanted into the recipient, a rejection response by the recipient to the donor cells is inhibited and the recipient is tolerized to the donor organ or cell. Alternatively, a non-toxic DT mutant such as DTM2 or CRM197 can first be administered followed by the immunotoxin. This method can use any of the immunotoxins (e.g., anti-CD3-CRM9, scUCH1-DT390, etc.) or non-toxic-DT mutants described herein with the dosages and modes of administration as described herein or otherwise determined by the practitioner.

The present tolerance induction method can also include administering an immunosuppressant compound before, at the same time, or after the immunotoxin exposure step. The immunosuppressant compound can be cyclosporine (e.g., cyclosporine A) or other cyclophylins, mycophenolate moefitil (Roche), methyl prednisone, deoxyspergualin (Bristol Myers), FK506, other known immunosuppressants, or any combination thereof. It will be appreciated that certain of these immunosuppressants have major effects on cytokine release occurring in the peritransplant period that may aid in the induction of the tolerant state. The method of inducing immune tolerance can further comprise administering donor bone marrow at the same time or after the exposure step.

Any one, two, or more of these adjunct therapies can be used together in the present tolerance induction method. Thus, the invention includes at least six methods of inducing tolerance using immunotoxin (IT): (1) tolerance induction by administering IT alone; (2) tolerance induction by administering IT plus other drugs that alter immune function such as high dose corticosteroids; (3) tolerance induction by administering IT plus immunosuppressant drugs, such as mycophenolate mofetil and/or deoxyspergualin; (4) tolerance induction by administering IT plus other drugs that alter immune function, plus immunosuppressant drugs; (5) tolerance induction by administering IT and bone marrow; and (6) tolerance induction by administering IT plus bone marrow, plus immunosuppressant drugs. The adjunct therapy can be administered before, at the same time or after the administration of immunotoxin. Different adjunct therapies can be administered to the recipient at different times or at the same time in relation to the transplant event or the administration of immunotoxin, as further described below.

Because the immunosuppressant can be administered before the immunotoxin and/or other treatments, the present method can be used with a patient that has undergone an organ transplant and is on an immunosuppressant regimen. This presents a significant opportunity to reduce or eliminate traditional immunosuppressant therapy and its well documented negative side-effects. Also, as described below, treatment with immunosuppressants prior to transplantation could be particularly useful in cadaveric and xenogeneic transplants. In such a setting of pre-transplant treatment with immunosuppressant, the administration of immunotoxin can be delayed for up to seven or more days post-transplantation.

An example of a schedule of immunotoxin and immunosuppressant administration for patients receiving organ transplants is as follows:

- day −24 to −0 hours: begin immunosuppressant treatment;
- day 0: perform transplant;
- day 0: immediately following transplant administer 1st immunotoxin dose;
- day 1: 2nd immunotoxin dose;
- day 2: 3rd and final immunotoxin dose.

Immunosuppressant treatment may end at day 3 or extend to day 14. Immunosuppressant treatment is also effective if begun at the time of transplantation, and can continue for up to two weeks after transplantation.

The presently preferred doses of the immunotoxin are those sufficient to deplete peripheral blood T-cell levels to 80%, preferably 90% (or especially preferably 95% or higher) of preinjection levels. This should require mg/kg levels for humans similar to those for monkeys (e.g., 0.05 mg/kg to 0.3 mg/kg body weight), which toxicity studies indicate should be well tolerated by humans. Thus, the immunotoxin can be administered to safely reduce the recipients T cell population.

EXAMPLE 1

Establishment of Tumors

The experimental design of the studies that give rise to the present invention was dictated by the goal of having an animal model as closely relevant to human in vivo tumor therapy as possible. In order to minimize the host killer cell immune response, bg/nu/xid strain of nude mice were used Camel-Reid and Dick (1988) *Science* 242:1706). The human T cell leukemia cell line, Jurkat, was chosen because of previous studies with this line and its relatively normal average complement of CD3 receptors (Preijers et al. (1988) *Scand. J. Immunol.* 27:553). The line was not cloned so that receptor variation among individual cells existed a scheme was developed whereby well established tumors of constant mass equal to 0.1% of body weight ($\approx 4\times10^7$ cells) could be achieved 7 days after inoculation of Jurkat cells (see Dillman et al. (1988) *Cancer Res.* 15:5632). This required prior irradiation and inoculation with lethally irradiated helper feeder cells (see Dillman et al. (1988) *Cancer Res.* 15:5632).

Nude mice bg/nu/xid maintained in a semi-sterile environment are preconditioned with 400 cGy whole body $^{137}$CS γ radiation on day −7. On day 0, 2.5×10$^7$ Jurkat cells (human T cell leukemia CD3+, CD4+, CD5+) are injected subcutaneously with 1×10$^7$ HT-1080 feeder cells (human sarcoma) which have received 6000 cGy. Jurkat cells were passaged every other week in mice as subcutaneous tumors and dissociated by collagenase/dispase prior to inoculation. This cell population exhibits a 40% inhibition of protein synthesis after 5 hours exposure to 10$^{11}$ M anti-CD3-DT. Clones isolated from this population by infinite dilution exhibit varying sensitivity to anti-CD3DT (4 less sensitive, 3 more sensitive) corresponding to a 1.5 log variation in dose response curves. immunotoxin treatment is given by intraperitoneal injection starting on day 7 when the tumor is visibly established. Evaluation takes place on day 37.

EXAMPLE 2

Guinea Pig Studies

Immunotoxin toxicity studies were performed in guinea pigs, an animal (like humans) with a high sensitivity to diphtheria toxin (mice are highly resistant to diphtheria toxin). Therapy of CRM9 conjugates was set at ½ the guinea pig minimum lethal dose. In this study, minimum lethal dose (MLD) is defined as the minimum tested dose which results in both non-survivors and survivors over a 4 week evaluation period. All animals survive when a MLD is reduced by 0.5. MLD was evaluated in guinea pigs (300–1000 g) by subcutaneous injection. The following MLDs were found and are listed as μg of toxin/kg body weight; DT, 0.15; CRM9, 30; anti-CD5-DT (cleavable), 0.65; anti-CD5-CRM9 (non-cleavable), 150. Finally, the therapeutic efficacy of the immunotoxin treatment in producing tumor regressions was compared to graded doses of whole body irradiation which resulted in similar tumor regressions.

EXAMPLE 3

Comparison of Immunotoxins

Several types of immunotoxins were compared in this study. They were synthesized as previously described by thiolating both the monoclonal antibody moiety and the toxin moiety and then crosslinking the bismaleimide crosslinkers (Neville et al. (1989) *J. Biol. Chem.* 264: 14653). Purification was performed by size exclusion HPLC columns and fractions containing 1:1 toxin:antibody mol ratios were isolated for these studies. Conjugates made with an acid-labile crosslinker bismaleimidoethoxy propane were compared with a non-cleavable, bismaleimidohexane. Conjugates made with this cleavable crosslinker have been shown to hydrolyze within the acidifying endosome releasing free toxin moieties with half-times of hydrolysis measured at pH 5.5 of 36 min (Neville et al. (1989) *J. Biol. Chem.* 264:14653).

The results of this study are tabulated in Table I. Non-treatment groups such as group 10, groups treated with anti-CD5 immunotoxins (groups 5 and 6), and group 4 treated with a mixture of anti-CD3 and CRM9 did not show regression. The vascularized tumor nodules that weighed 20 mg on day 7 grew to between 1.5 to 7.8 g on day 37 and weighed between 7.9 and 11.6 on day 56. No late spontaneous regressions were noted. In contrast, group 1 consisting of treatment with anti-CD3-CRM9 non-cleavable conjugate (NC) given at 25 μg/kg on days 7, 8, and 9 showed only 1 tumor out of 6 by day 37. Some of the remaining animals were subject to autopsy and they failed to reveal residual tumor or even scaring. Tumors identified as regressed on day 37 by superficial inspection did not reappear during the course of the study (56 days).

TABLE 1

IMMUNOTOXIN AND RADIATION TREATMENT ON SUBCUTANEOUS HUMAN T CELL TUMORS (JURKAT) IN NUDE MICE

| Group | Treatment | Dose (intraperitoneal) | Animals Bearing Tumors At Day 37/Group Animals | % Tumor Regressions |
|---|---|---|---|---|
| 1 | Anti-CD3-CRM9 (NC)* | 25 μg/kg. × 3d | 1/6 | 83 |
| 2 | Anti-CD3-CRM9 (NC) Anti-CD5-CRM9 (C) | 19 μg/kg. × 2d 19 μg/kg. × 2d | 1/4 | 75 |
| 3 | Anti-CD3-CRM9 (C) | 25 μg/kg. × 3d | 2/4 | 50 |
| 4 | Anti-CD3 + CRM9 | 25 μg/kg. × 3d | 4/4 | 0 |
| 5 | Anti-CD5-CRM9 (C) | 25 μg/kg. × 3d | 5/5 | 0 |
| 6 | Anti-CD5-DT (NC) | 25 μg/kg. × 1d | 9/9 | 0 |
| 7 | γradiation $^{137}$Cs | 400 cGy | 2/2 | 0 |
| 8 | γradiation $^{137}$Cs | 500 cGy | 3/6 | 50 |
| 9 | γradiation $^{137}$Cs | 600 cGy | 0/2$^b$ | 100 |
| 10 | None | | 6/6 | 0 |

*Anti-CD3 refers to the monoclonal antibody UCHT1 and was purchased from Oxoid USA, Inc. Anti-CDS refers to the monoclonal antibody T101 and was a gift from Hybritech (San Diego). NC and C refer, respectively, to non-cleavable and cleavable conjugates.
$^b$These animals were evaluated on days 10 and 13 at the time of death from radiation sickness.

The cleavable crosslinker confers no therapeutic advantage to anti-CD3-CRM9 immunotoxins and may be less effective (group 3). Cleavable crosslinkers confer some advantage with anti-CD5-CRM9 conjugate in vitro (5) but had no effect in this in vivo system (group 5), and lacked significant potentiating effect when administered with anti-CD3-CRM9 (group 2). The cleavable crosslinker conferred a marked therapeutic advantage to anti-CD5 wild type toxin conjugates and tumor regressions were achieved. However, in these cases the guinea pig toxic dose was exceeded, a single dose on day 7 of cleavable anti-CD5-DT at 6 μg/kg produced 8/10 tumor regressions while a cleavable conjugate made with an irrelevant antibody (OX8) produced no regressions (4/4). However, this dose exceeded the guinea pig MLD by 9 fold a rescue strategy was tried in which the above conjugate dose was given intravenously followed by DT antitoxin 4 hours later (also intravenously). The 4 hr rescue could not raise the MLD above 0.65 µg/kg. The 1 hr rescue could not raise the MLD above 0.65 µg/kg. The 1 hr rescue raised the MLD to 36 µg/kg, however, there were no tumor regressions in 10 mice receiving 21.5 µg/kg of the cleavable anti-CD5-DT conjugate.

In groups 7–9 increasing single doses of whole body radiation (102 cGy/min) were given to animals bearing 3×3×5 mm tumors. At 400 cGy no complete regressions occurred. At 500 cGy 50% complete tumor regressions occurred. At 600 cGy 100% regression was achieved as judged on day 10 and 13 when the animals died from radiation sickness. (Groups 7–9 did not receive prior radiation and tumor takes were less than 100%). It appears that the 75 µg/kg anti-CD3-CRM9 (NC) immunotoxin is equal in therapeutic power to between 500 and 600 cGy of radiation.

EXAMPLE 4

Estimation of Cell Kill

The actual cell kill achieved by the radiation and the immunotoxin can be estimated by assuming radiation single hit inactivation kinetics along with a $D_{37}$ value for the radiation a value for $D_{37}$, of 70–80 cGy with n=1.2–3 is not unreasonable for a rapidly dividing helper T cell. $D_{37}$ is the dose of radiation which reduces the fraction of surviving cells to 1/e as extrapolated from the linear portion of the log survivors vs. dose curve and n is the intercept at 0 dose (Anderson and Warner (1976) in *Adv. Immunol.*, Academic Press Inc., 24:257). At a dose of 550 cGy the fraction of surviving cells is calculated to be about $10^3$. Since a majority of tumors completely regress at this dose we estimate that both therapies are producing an approximate 3 log kill. (The remaining cells, $4\times10^7\times10^3=4\times10^4$ cells apparently cannot maintain the tumor, i.e., the in vivo plating efficiency is low, a fairly typical situation in the nude mouse xenograft system.) The reliability of this 3 log kill estimate has been verified by determining the tissue culture plating efficiency by limiting dilution of 7 day established Jurkat tumors (following dispersal) and tumors exposed 18 hours earlier in vivo to 600 cGy. Plating efficiencies were 0.14 and $1.4\times10^4$, respectively. (Plating efficiency is the reciprocal of the minimum average number of cells per well which will grow to form one colony.

It should be emphasized that with high affinity holo-immunotoxins the cell kill is inversely proportional to the target cell number. This presumably occurs because receptors are undersaturated at tolerated doses and free conjugate concentration falls with increasing target cell burden Marsh and Neville (1987) *Ann. N.Y. Acad Sci.* 507:165; Yan et al. (1991) *Bioconjugate Chem.* 2:207). To put this in perspective, the tumor burden in this study is almost equal to the number of T cells in a mouse ($\approx 10^8$). It can be expected that a tolerated dose of anti-CD3-CRM9 immunotoxin can achieve an in vivo 3 log depletion of a normal number of CD3 positive T cells.

EXAMPLE 5

T-Cell Depletion in Rhesus Monkeys Induced by FN18-CRM9

FN18-CRM9 Conjugate

The monoclonal antibody FN18 is the monkey equivalent of the human anti-CD3 (UCHT1) and is known to bind the same CD3 receptor epitopes ($\in$ and $\gamma$) as bound by the human CD3 antibody and is the same isotype as the human CD3 antibody. Thus, in terms of the parameters relevant for predicting successful T cell depletion, the present CD3-CRM9 conjugate and FN18-CRM9 are expected to have the same activity.

Administration

Conjugates can be administered as an I.V. bolus in a carrier consisting of 0.1 M $Na_2SO_4$+0.01 M phosphate buffer, pH 7.4. The dose schedule is every other or third day for about 3 days. The total dose is preferably from 50 to 300 micrograms of toxin per kg of body weight.

The actual dose of FN18-CRM9 used was varied between 0.167–1.13 of the minimum lethal dose (MLD) in guinea pigs. Since the estimation of the MLD was performed in an animal lacking an immunotoxin target cell population (guinea pigs), the true MLD of FNI8-CRM9 and anti-CD3-CRM9 is expected to be higher in monkeys and humans than in guinea pigs.

T Cell Kill

Helper T cell (CD4+cells) numbers in peripheral blood fell dramatically after the initial administration of FN18-CRM9 in two rhesus monkeys. T cell counts began to rise by day 4 (sampled just prior to the second dose of FN18-CRM9). On day 5 in monkey 8629, CD4+ cells were depressed below the limit of detection (<50 cells/mm³). Cells remained below or equal to 200/mm³ out to day 21. This low level of CD4+ cells is associated with profound immunodeficiency in humans and in monkeys (Nooij and Jonker (1987) *Eur. J. Immunol.* 17:1089–1093). The remarkable feature of this study is the long duration of helper T cell depletion (day 21) with respect to the last administration of immunotoxin (day 4) since intravenously administered immunotoxins were cleared from the vascular system with half-lives <9 hours (Rostain-Capaillon and Casellas (1990) *Cancer Research* 50:2909–2916), the effect outlasting circulating immunotoxin. This is in contrast to T cell depletion induced by unconjugated anti-CD3 antibodies (Nooij and Jonker (1987) *Eur. J. Immunol.* 17:1089–1093).

In monkey IWS the second dose of conjugate only appeared to result in a diminished rate of CD4+ cell recovery. However, CD4+ cells were still fewer than normal at day 21. The blunted response of monkey 1WS to the second dose of immunotoxin was found to be due to a preexisting immunization of this animal to the toxin. Monkey 1WS had a significant pre-treatment anti-diphtheria toxin titer as revealed by a Western blot assay. This titer was markedly increased at day 5, indicative of a classic secondary response. In contrast, monkey 8629 had no detectable pre-treatment titer and only a trace titer by day 5 and a moderate titer by day 28.

The specificity of FN18-CRM9 toward T cells can be seen by comparing the total white blood cell (WBC) count in the same two monkeys. WBCs fell, but only to 45% of baseline value on day 2 compared to 6% of baseline values for the CD4+ T cell subset. Most of the fall in WBC values can be accounted for by the T cell component of the WBC population ($\approx 40\%$). However, B cells are initially depleted after FN18-CRM9 although these cells recover more quickly. FN18 is an IgG, isotype and as such is known to bind to $Fc_H$ receptors present on B cells and macrophages with low affinity. The FN18-CRM9 depletion of B cells indicates that significant interactions between the Fc portion of the FN18 antibody and B cells is taking place.

The peripheral T cell depletion induced by unconjugated FN18 at a dose known to produce immunosuppression 0.2 mg/kg/day (Nooij and Jonker (1987) *Eur. J. Immunol.* 17:1089–1093) was compared to the immunotoxin FN18-CRM9 administered at ⅛th the FN18 dose. Peripheral CD4+ T cell depletion is more pronounced and more long-lasting with the conjugate. The demonstration that FN18-CRM9 reduces peripheral helper T cell subset (CD4+) to levels less than or equal to 200 cell/mm³ for a period as long as 21 days demonstrates that this immunotoxin and its anti-human analogs are effective immunosuppressive reagents.

The demonstration that FNI18-CRM9 is a potent agent for inducing T cell depletion in non-human primates demonstrates that an anti-human homolog of FN18-CRM9, UCHT1-CRM9 (Oxoid USA, Charlotte, N.C.) for example, is a potent agent for inducing T cell depletion in humans.

The Fc binding region of anti-TCR/CD3 monoclonals may or may not be needed to induce T cell depletion when the anti-TCR/CD3 monoclonals are conjugated to CRM9. The $Fc_{II}$ binding regions can be removed, for example, by forming the conjugates with F(ab')$_2$ derivatives as is indicated in the literature (Thorpe et al. (1985) *J. Natl. Cancer Inst.* 75:151–159). In addition, anti-TCR/CD3 IgA switch variants such as monoclonal antibody T3, a may be used (Ponticelli et al. (1990) *Transplantation* 50:889–892). These avoid rapid vascular clearance characteristic of F(ab')$_2$ immunotoxins. F(ab')$_2$ and IgA switch variants of anti-TCR/CD3-CRM9 immunotoxins are therefore derivative anti-TCR/CD3 immunotoxins. These derivatives will avoid the B cell interaction noted and can increase specificity. However, $IgG_{2a}$, switch variants will maximize T cell activation through the $F_r$ receptor and may be useful in certain situations where T cell activation aids immunotoxin induced toxicity.

General methods to make antibodies lacking the Fc region or to make antibodies which are humanized are set forth in Harlow and Lane, Antibodies: a Laboratory Manual, Cold Spring Harbor Laboratory, Cold Spring Harbor, New York, 1988. Thus, as used in the claims, antibody can mean the entire antibody or any portion of the antibody sufficient for specific antigen or receptor binding.

EXAMPLE 6

An anti-CD3 Single-chain Immunotoxin with a Truncated Diphtheria Toxin Decreases Inhibition by Pre-existing Antibodies in Human Blood The present Example examines the effect of human serum with pre-existing anti-DT antibodies on the toxicity of UCHT1-CRM9, an immunotoxin directed against CD3 molecules on T-lymphocytes. Sera with detectable anti-DT antibodies at 1:100 or greater dilutions inhibited the immunotoxin toxicity. Experiments with radiolabeled-UCHT1-CRM9 indicate that anti-DT antibodies partially block its binding to the cell surface as well as inhibit the translocation from the endosome to the cytosol. The inhibitory effect could be adsorbed using a full-length DT mutant or B-subfragment. A C-terminal truncation mutant could not adsorb the inhibitory effect, suggesting that the last 150 amino acids contain the epitope(s) recognized by the inhibitory antibodies.

Therefore, an anti-CD3 single-chain immunotoxin, sFv-DT390, was made with a truncated DT. The $IC_{50}$ of sFv-DT390 was $4.8 \times 10^{-11}$ M, ¹⁄₁₆ the potency of the divalent UCHT1-CRM9. More importantly, as shown in Table 2, sFv-DT390 toxicity was only slightly affected by the anti-DT antibodies in human sera. "sFv" and "scUCHT1" both are singe chain antibodies containing the variable region.

TABLE 2

Anti-DT antibodies present in human sera have reduced effect on sFv-DT390 toxicity.

| | | Protein syntheses (% Control) | | | | | |
|---|---|---|---|---|---|---|---|
| | ELISA value | UCHT1CRM9 | | | sFv-DT390 | | |
| Serum Sample | (±S.D.) | 1:10 | 1:10² | 1:10³ | 1:10 | 1:10² | 1:10³ |
| 10012 | 0.491 ± 0.025 | 119 ± 24 | 8 ± 2 | ND$^a$ | 47 ± 9 | 21 ± 8 | ND |
| Pooled | 0.331 ± 0.015 | 108 ± 37 | 7 ± 1 | ND$^a$ | 49 ± 7 | 16 ± 7 | ND |
| Goat | 1.450 ± 0.013 | ND | ND | 94 ± 21 | ND | ND | 8 ± 11 |

$^a$Not done
UCHT1CRM9 or sFv-DT390 (2 × 10⁻⁹M) was incubated with the indicated dilutions of serum for 30 min. The mixture was then added to Jurkat cells as described. The final concentration of immunotoxin on cells was 1 × 10⁻¹⁰M. Four replicates were performed for each sample. Data are presented as a mean value ± S.D. in percentage of the control counts. UCHT1-CRM9 inhibited protein synthesis to 5% of controls while the sFv-DT390 inhibited protein synthesis to 18% of controls. The ELISA value was determined using a 1:100 dilution of serum. The results are representative of two independent experiments.

EXAMPLE 7

Expression and Characterization of a Divalent Chimeric Anti-human CD3 Single Chain Antibody Murine anti-CD3 monoclonal antibodies (mAbs) are used in clinical practice for immunosuppression. However, there are two major drawbacks of this treatment: the associated cytokine release syndrome and human anti-mouse antibody response. To overcome these side effects, a chimeric anti-human CD3 single chain antibody, scUCHT1 was generated. It is an IgM variant of the UCHT1 as described. scUCHT1 consists of the light and heavy variable chain binding domains of UCHT1 and a human IgM Fc region (μCH2 to μCH4). The method used was reported by Shu et al. (37) and is further described below. The following data show that the engineered chimeric anti-CD3 single chain antibody (scUCHT1) will be useful in clinical immunosuppressive treatment.

Oligonucleotide Primers and DNA Amplification.

Primers used for the antibody engineering are listed in Table 3, and the primer sequences are based on published data (13). mRNA isolated from UCHT1 hybridoma cells (provided by Dr. P. C. Beverley, Imperial Cancer Research Fund, London was reverse transcribed into cDNA The VL and VH regions of UCHT1 were amplified with polymerase chain reaction (PCR) from the cDNA using primer pairs P1, P2 and P3, P4 respectively. Primers P2 and P3 have a 25 bp complementary overlap and each encoded a part of a linker peptide (Gly4Ser)3. The single chain variable fragment (VL-linker-VM was created by recombinant amplification of VL and VH using primers P1 and P4, a mouse kappa chain signal sequence was added at the VL 5'-end by PCR, first with primers SP2 and P4, and then with primers SP1 and P4. The human IgM Fc region (μCH2 to μCH4) was amplified from the plasmid pBlue-huIgM (kindly provided by Dr. S. V. S. Kashmiri, National Cancer Institute, Bethesda. This gene fragment was about 1.8 kb. The VL-linker-VH-μCH2 region which is important for antigen recognition was confirmed by sequence analysis. Finally, the single chain variable fragment and the human IgM Fc region were cloned into plasmid pBK/CMV (Stratagene, La Jolla, Calif., USA). Using the generated pBK/scUCHT1 plasmid as template, an in vitro transcription-translation assay yielded a product of 75 kDa, the expected size.

lyzed by immunoblotting using anti-human IgM antibody. Human IgM antibody was included as a control in the analysis. Under reducing conditions, scUCHT1 produced by COS-7 and SP2/0 cells had a similar electrophoretic mobility to that of the control human IgM heavy chain (75 kDa). Under non-reducing conditions, scUCHT1 from COS-7 cells appeared as a single band of approximately 150 kDa, which was thought to be a homodimer of the single chain antibody. SP2/0 cells mainly produced a protein of similar size with some higher molecular weight products.

In constructing scUCHT1, the domain orientation of sFv, VH-VL, which Shu et al. used to VL-VH orientation, was changed so that the heavy chain constant domains were linked to the VH domain. In mammalian cells, secretion of immunoglobulin molecules is mediated by light chain, and free light chain is readily secreted (38). However, free heavy chain is generally not secreted (39). In a bacterial expression system, the yield of secreted sFv with a VL-VH domain orientation was about 20-fold more than that obtained with a VH-VL domain orientation (40). It was reasoned that VL at the NH2-terminal position and VH linked to heavy chain constant region in scUCHT1 construct might enhance the secretion of this immunoglobulin-like molecule in mammalian cells. In fact scUCHT1 was efficiently produced by both COS-7 and SP2/0 cells. Hollow fiber culture should increase its production. Moreover, scUCHT1, the IgM-like molecule,

TABLE 3

Sequences of oligonucleotide primers used for PCR amplification

| Primers | Sequences | RE sites |
|---|---|---|
| | 5'                              3' | |
| P1(UCHT1 VL5) | GACATCCAGATGACCCAGACC (SEQ ID NO:1) | |
| P2(UCHT1 VL3) | CCTCCCGAGCCACCGCCTCCGCTGCCTCCGCCTCCTTTTATCTCCAGCTT G(T)GTC(G)CC (SEQ ID NO:2) | |
| P3(UCHT1 VH5) | GCAGCGGAGGCGGTGGCTCGGGAGGGGGAGGCTCGGAGGTGCAGCTTC AGCAGTCT (SEQ ID NO:3) | |
| P4(UCHT1 VH3) | GC<u>AAGCTT</u>GAAGACTGTGAGAGTGGTGCCTTG (SEQ ID NO:4) | Hind III |
| P5(HuIgM-CH2) | GTCTCTTCA<u>AAGCTT</u>ATTGCC(T)GAGCTGCCTCCCAAA (SEQ ID NO:5) | Hind III |
| P6(HuIgM-CH4) | GCA<u>TCTAGA</u>TCAGTAGCAGGTGCCAGCTGTGT (SEQ ID NO:6) | Xba I |
| SP1 (Signal 1) | CG<u>GTCGAC</u>ACCATGGAGACAGACACACTCCTGTTATGGGTACTGCTGCT CTGGGTTCCA (SEQ ID NO:7) | Sal I |
| SP2 (Signal 2) | GTACTGCTGCTCTGGGTTCCAGGTTCCACTGGGGACATCCAGATGACCC AG (SEQ ID NO:8) | |

Expression in COS7 and SP2/0 Cells.

The gene fragment encoding scUCHT1 was then cloned into an expression vector pLNCX (36). The scUCHT1 gene construct was introduced into COS-7 cells with a calcium-phosphate method (32), and introduced into SP2/0 myeloma cells by electroporation (33). Cells transfected were selected with 500 μg/ml G418 (GIBCO/BRL, Gaithersburg, Md., USA) in DMEM medium. The drug resistant transfectants were screened for scUCHT1 secretion by an anti-human IgM ELISA technique. Transfectants secreting scUCHT1 were cloned by limiting dilution.

Two stable clones, COS-4C10 and SP2/0-7C8, which could produce about 0.5 mg/ml scUCHT1 in culture medium, were selected for further evaluation. The culture supernatant of COS-4C10 and SP2/0-7C8 cells was anahas a secretory tailpiece with a penultimate cysteine (Cys 575) which is involved in polymerization and also provides retention and degradation of IgM monomers (41–43). Replacing the Cys 575 with serine might also greatly improve the yield.

scUCHT1 secreted from COS-7 cells was shown to be a divalent form by immunoblotting, suggesting a disulfide bond linkage of two monovalent molecules. The disulfide bond is likely situated between the μCH2 and γCH3 regions, where the Cys 337-Cys 337 disulfide bond is thought to exist. Cys 337 is believed to be sufficient for assembly of IgM monomers, and was neither sufficient nor necessary for formation of polymers. However, Cys 575 was necessary for assembly of IgM polymers, and Cys 414 was not required for formation of IgM monomers or polymers (44). This divalent form of the single chain antibody should increase its binding affinity. While scUCHT1 produced from SP2/0 cells was mainly in the divalent form, a small fraction of the antibody had a higher molecular weight, nearly comparable to that of the human IgM pentamer, the natural form of secreted human IgM.

Western Blotting Analysis of scUCHT1.

scUCHT1 was precipitated from the culture supernatant using goat anti-human IgM-Agarose (Sigma, St. Louis, Mo., USA), and separated on 4–20% SDS-PAGE gradient gel under reducing and non-reducing conditions. The separated proteins were transferred to ProBlottTM membrane (Applied Biosystems, Foster City, Calif., USA) by electroblotting at 50 volts for 1 hour. The membrane was blocked and incubated with alkaline phosphatase labeled goat anti-human IgM antibody (PIERCE, Rockford, Ill., USA) following the manufacturer's instruction. Color development was carried out with substrate NBT/IBCIP (PIERCE).

Purification of scUCiHT1

Culture supernatant was mixed with anti-human IgM-Agarose, and incubated at 4° C. with shaking overnight, and then the mixture was transferred to a column. The column was washed with washing buffer (0.01 M Na-phosphate, pH 7.2, 0.5 M NaCl) until the OD280 of flow-through was <0.01. scUCHT1 was eluted with elution buffer (0.1 M glycine, pH 2.4, and 0.15 M NaCl). The fractions were neutralized with 1 M Na-phosphate (pH 8.0) immediately, and then concentrated and dialyzed against PBS.

Competitive Binding Assay

The parental antibody UCHT1 was iodinated using Bolton-Hunter Reagent (NEN, Wilmington, Del., USA) as described previously (34). The $^{125}$I-labeled UCHT1 was used as tracer and diluted with DMEM medium to 0.3–0.6 nM. UCHT1 and the purified scUCHT1 from COS-7 and SP2/0 transfectant cells were used as competitors. Human CD3 expressing Jurkat cells were suspended in DMEM medium ($2\times10^7$/ml). 50 µl of such cell suspension ($1\times10^6$) was incubated with 50 µl diluted tracer and 50 ml diluted competitors on ice for 2 hours. Afterwards, cells were pelleted, and counted in a gamma counter. Results were expressed as a percentage of the $^{125}$I-UCHT1 bound to cells in the absence of competitors.

scUCHT1 from both COS-7 and SP2/0 cells could specifically inhibit the binding of $^{125}$I-UCHT1 to Jurkat cells in a dose dependent way. As the concentration of the competitors (UCHT1, scUCHT1 from COS-7 and SP2/0 cells) increased from 1 to 100 nM, the tracer (125I iodinated UCHT1) bound to Jurkat cells decreased from 80% to nearly 0%. No significant difference was observed among the affinity curves of UCHT1 and scUCHT1 from COS-7 and SP2/0 cells. This indicates that the engineered antibody scUCHT1 has nearly the same affinity as UCHT1. Moreover, scUCHT1 contains human IgM constant region, and is expected be less immunogenic than UCHT1. The degree of its immunogenicity might vary due to the murine variable region of scUCHT1. Humanized variable regions by CDR-grafting or human variable regions can be used to further reduce its immunogenicity (31).

T-cell Proliferation Assay.

T-cell proliferation in response to UCHT1 and scUCHT1 was tested on human PBMCs from a healthy donor. Human peripheral blood mononuclear cells (PBMCs) were isolated from blood of a healthy adult by density centrifuge over Ficoll-Hypaque gradient (34). The PBMCs were resuspended in RPMI 1640 supplemented with 10% FCS and aliquoted to 96-well U-bottom plates at $5\times10^4$ cells/well. Increasing amounts of anti-CD3 antibodies (UCHT1, scUCHT1) were added. After 72 hours of culture at 37° C. in a humidified atmosphere containing 5% $CO_2$, 1 µCi [$^3$H]thymidine (NEN) was added to each well. Sixteen hours later, cells were harvested and [$^3$H]thymidine incorporation was counted in a liquid scintillation counter.

The parental antibody UCHTl1 started to induce proliferation at 0.1 ng/ml, and peaked at 100 ng/ml, a small drop in CPM was observed as the concentration increased to 1,000 ng/ml. However, [$^3$H]thymidine incorporation in PBMCs incubated with scUCHT1 was only slightly increased in the range of 0.1–10 ng/ml, and when the concentration was higher than 10 ng/ml, the incorporated counts decreased and were close to 0 counts at 1000 ng/ml.

Measurement of TNF-α and IFN-γ

TNF-α and IFN-γ productions of human PBMCs induced by UCHT1 and scUCHT1 were measured with ELISA. $4\times10^5$ PBMCs were cultured with serial dilutions of anti-CD3 antibodies (UCHT1, scUCHT1) in 96-well flat-bottom plates in RPMI 1640 supplemented with 10% FCS. Supernatant was collected at 36 hours for TNF-α and 72 hours for IFN-γ after the start of the culture (35). TNF-α and IFN-γ were measured with ELISA kits (Endogen Inc. Cambridge, Mass., USA) following the manufacturer's instruction.

The native antibody UCHT1 induced production of both TNF-α and IFN-γ in a dose dependent way. Higher concentration of UCHT1 induced higher production of TNF-α and IFN-γ. On the contrary, scUCHT1 did not induce secretion of TNF-α at any concentration, and inhibited IFN-γ production when its concentration was higher than 0.1 ng/ml. At the time of supernatant harvesting, the PBMCs cultured with UCHT1 and scUCHT1 were also checked with trypan blue exclusion test. Cells were shown to be alive in both situations. In TNF-α and IFN-γ ELISA assays, an unrelated human IgM was included and it did not affect the TNF-a and IFN-g production.

Measurement of Possible Complement Binding by scUCHT1

Divalent scUCHT1 failed to bind detectable quantities of complement. This feature is an advantage in treating patients with a foreign protein in that it will minimize immune complex disease.

Anti-CD3 mAbs can induce T cell activation and proliferation both in in vitro and in vivo situations (45). Crossing-linking of anti-CD3 antibody between T cells and FcR expressing cells is an essential step in this process (46). T cell activation therefore reflects an efficient interaction of the mAb with a human FcR. Previous data of in vitro study indicated that T cell activation resulted in increased production of TNF-α, IFN-γ, and IL-2 (24). Human IgG Fc receptors (FcγR I, FcγR II, FcγR III) are distributed on human monocytes, T, B lymphocytes, and NK cells (47). FcγR I and FcγR II can recognize both mouse and human IgG. In accordance with the above observation, UCHT1 was potent in induction of T cell proliferation and TNF-α and IFN-γ release. Human IgM Fc receptor (FcµR) was reported to be present mainly on a small fraction of B lymphocytes, NK cells, and possibly a helper subset of T lymphocytes (47, 48). Pentamer form of IgM and an intact γCH3 domain are required for optimal binding to FcµR. Monomeric or dimeric subunits of IgM are less efficient in binding to FcµR (49, 50). Cross-linking of IgM to FcµR on T cells inhibited the mitogen-induced T cell proliferation, and FcµR may function as a negative signal transducing molecule (51, 52).

Therefore, it can specifically bind to human CD3 molecule and FcµR. It is conceivable that scUCHT1 can cross-link human B and T cells, and possibly T and T cells. In an in vitro assay, scUCHT1 from both COS-7 and SP2/0 cells had little effect in the T cell proliferation assay at low concentrations (below 10 ng/ml), and became inhibitory as the concentration increased. In accordance with these results, scUCHT1 did not induce TNF-α production and even inhibited the basal yield of IFN-γ.

The present chimeric anti-CD3 single chain antibody scUCHT1 possesses high human CD3 binding specificity and affinity, and does not induce T cell proliferation and cytokine release. Moreover, it has a human IgM Fc fragment, which should decrease the possibility of inducing human anti-mouse antibody response. Thus, scUCHT1 can be used for clinical immunosuppressive treatment.

EXAMPLE 8

Immunotoxin Plus Short Term Immunosuppressant Drugs Induces Tolerance in Monkeys in Models Simulating Human Cadaveric Donors Immunotoxin Techniques for preparing anti-CD3-CRM9 (where the antibody is directed at the human T-cell receptor complex "CD3") have previously been described. See U.S. Pat. No. 5,167,956 and D. Neville et al., 89 P.N.A.S. USA 2585-2589 (1992), a hybridoma secreting UCHT1 was kindly provided by Dr. Peter Beverly, Imperial Cancer Research Fund, and was grown in ascites fluid and purified over immobilized Protein a. This is an IgGl.

FN18, also an IgGl, is the rhesus analog of UCHT1 and shares with it the property of being a T-cell mitogen in the presence of mixed mononuclear cells. FN18 was produced in hollow fiber and purified over Protein a. The strain of C. diphtheriae used for production of CRM9, C7 (βh tox-201 tox-9 h') was obtained from R. Holmes, Uniformed Services University of Health Sciences, Bethesda, Md. See also V. Hu et al., 902 Biochimicia et Biophysica Acta 24–30 (1987).

Antibody-CRM9 was recovered from the supernatant of 30 liter fermentation runs under careful control of iron concentration. See S. L. Welkos et al., 37 J. Virol. 936–945 (1981). CRM9 was purified by membrane concentration, ammonium sulfate precipitation and chromatography over DEAE. See S. Carroll et al., 165 Methods In Enzymology 68 (1988).

Large scale purification of immunotoxin was accomplished by HPLC size exclusion chromatography on MODcol (1266 Andes Blvd., St. Louis, Mo. 63132) 2"×10" column packed with Zorbax (DuPont Company) GF-250 5 µm, 150 Å. Fractions containing 1:1 toxin:antibody mol ratios were isolated for these studies.

Immunotoxins were synthesized as previously described by thiolating both the monoclonal antibody moiety and the toxin moiety and then crosslinking with bismaleimidohexane. See D. Neville et al., 264 J. Biol. Chem. 14653–14661 (1989). CRM9 was nicked and the monomer (Carroll et al.) was isolated by the MODcol column described above prior to thiolation.

While CRM9 is a presently preferred mutant diphtheria toxin protein, other preferred embodiments include diphtheria mutants with a mutation in the DT binding region, such as DT390 (as described), should also be suitable (as the concept behind the immunotoxin is to replace the normal binding function with the antibody provided T-cell binding function, with minimal conformational change).

T-Cell Ablation

Monoclonal antibody FN18 (specific for rhesus monkey T lymphocytes) coupled to the immunotoxin CRM9 was used to deplete peripheral blood T-cells to levels below 200 cells /M13 in adult rhesus monkeys (measured six days after the injection). Some modest B cell depletion occurred. Following depletion, complete T-cell recovery takes about three to four weeks in a juvenile rhesus monkey model using this agent. Surprisingly, notwithstanding this fast recovery, donor T-cells injected into the thymus still were not impaired in their ability to produce tolerance.

A group of rhesus monkeys undergoing mismatched renal transplantation received anti-CD3-CRM9 (IT) 18 hours pre-transplant, 0.067 mg/kg and 0.033 mg/kg on days 0 and +1. Group 1 received only IT, n=6. Group 2, n=7, received in addition to IT deoxyspergualin (DSG) IV 2.5 mg/kg/day and solumedrol (SM), 7, 3.5 and 0.33 mg/kg IV during the IT administration. DSG was continued from 4 to up to 14 days. Plasma samples were tested by ELISA for cytokine release syndrome by measuring pre and post transplant plasma IL-12 and INF gamma levels.

Graft Survival (Days)
Group 1 (IT alone) Group 2 (IT+DSG+SM)
10–57 n=6 (rejections) >155–200 n=4
28–45 n=3 (rejections)
2 deaths from non-rejection causes IT, Group I, (or rhesus anti-CD3 an antibody alone) elevated both IL-12 and INF-8 gamma. DSG and solumedrol appear to block IL-12 induced activation of INF-gamma by a mechanism that may be associated with NF-kappa/beta (FIG. 1). This treatment is found to eliminate peritransplant weight gain and serum hypoproteinemia, both signs of vascular leak syndrome, which in this study is associated with early graft rejection. This peritransplant treatment regimen can provide a rejection-free window for tolerance induction applicable to cadaveric transplantation.

It takes over 24 hours for IT to exert most of its lymph node T cell killing effects. Therefore, IT cadaveric transplantation protocols (protocols in which organ transplantation occurs generally within 6 hours of initial therapy and not longer than 18 hours) benefit substantially from peritransplant supplemental short term immunosuppressant agents to minimize peritransplant T cell responses to the new organ as shown by the above data.

EXAMPLE 9

Reversal of Diabetes in a Non-insulin Secreting Monkey.

Monkey 0038 is a non-obese 7 kg African Green monkey of 20 years of age who developed acute diabetic ketotic coma with a blood sugar of 950 mgm %. After resuscitation this monkey was found to require exogenous insulin to prevent life threatening hyperglycemia (4 units twice daily of a mixture of 70% NPH and regular human insulins). However, on this therapy blood sugars were elevated, between 200–480 mgm % and glycosylated hemoglobin was greater than 10%. Serum insulins were undetectable on 12 occasions when exogenous insulin injections were withheld for 48–72 hours. C-peptide levels were less than 0.4 ng/ml (0.9 ng/ml normal). The beta cell failure documented in this monkey is presumably a result of long term peripheral insulin resistance.

The islet donor for monkey 0038 was a normal juvenile rhesus monkey of between 2–3 years of age. Pancreas procurement was by standard technique for human multiple organ procurement. The preservation solution was that used by the University of Wisconsin at 4° C. Cold ischemia time was 6–8 hours. Islet isolation was the semi-automated technique described by Dr. C. Ricordi, using Liberase (8). Islet yield was 80,000 I.E., viability >90%. The islets were cultured overnight in RPMI 1640 at 37° C. with 10% normal monkey serum and 50,000 islets were transplanted the next day which is day 0. The transplant procedure was performed under anesthesia by a small midline abdominal incision, exposure and cannulation of the inferior mesenteric vein with a 5F feeding tube, and islet infusion by gravity into the portal vein via the inferior mesenteric vein.

Immune Tolerance Inducing Regimen day −1 and day +1: 0.1 mg/kg anti-rhesus anti-CD3-CRM9 (FN18-CRM9 chemical conjugate) (6,9).IV infusion over 3 minutes in 0.1 M Na2SO4+0.01M NaPO4, pH7.4 buffer.

day −1,0,1,2. Solumedrol (™) 15 mg/kg/IV infused in $V_2$ normal saline over 2.5 minutes starting 2 hrs prior to CD3-CRM9 on days −1 and 1.

day −1. Cyclosporine A, 20 mg/kg TV infused in ½ normal saline over 2.7 minutes.

day −1,0,1,2. Oral cyclosporine (Neoral, ™)120 mg/kg/day in 2 equally divided doses.

Immunotoxin Induced Blood T Cell Depletion Judged by %FN18+ Cells

CD3-IT 71% day 8 0% day 28 48% day 40 70%

(Pre-transplant anti-CRM9 titer in serum diluted 1:100 was positive at an ELISA O.D. of 0.146 or 2.2 times blank value. In spite of these antibodies directed at CD3-IT, significant T cell depletion was achieved)

Post Transplant Course

Figure 2A:
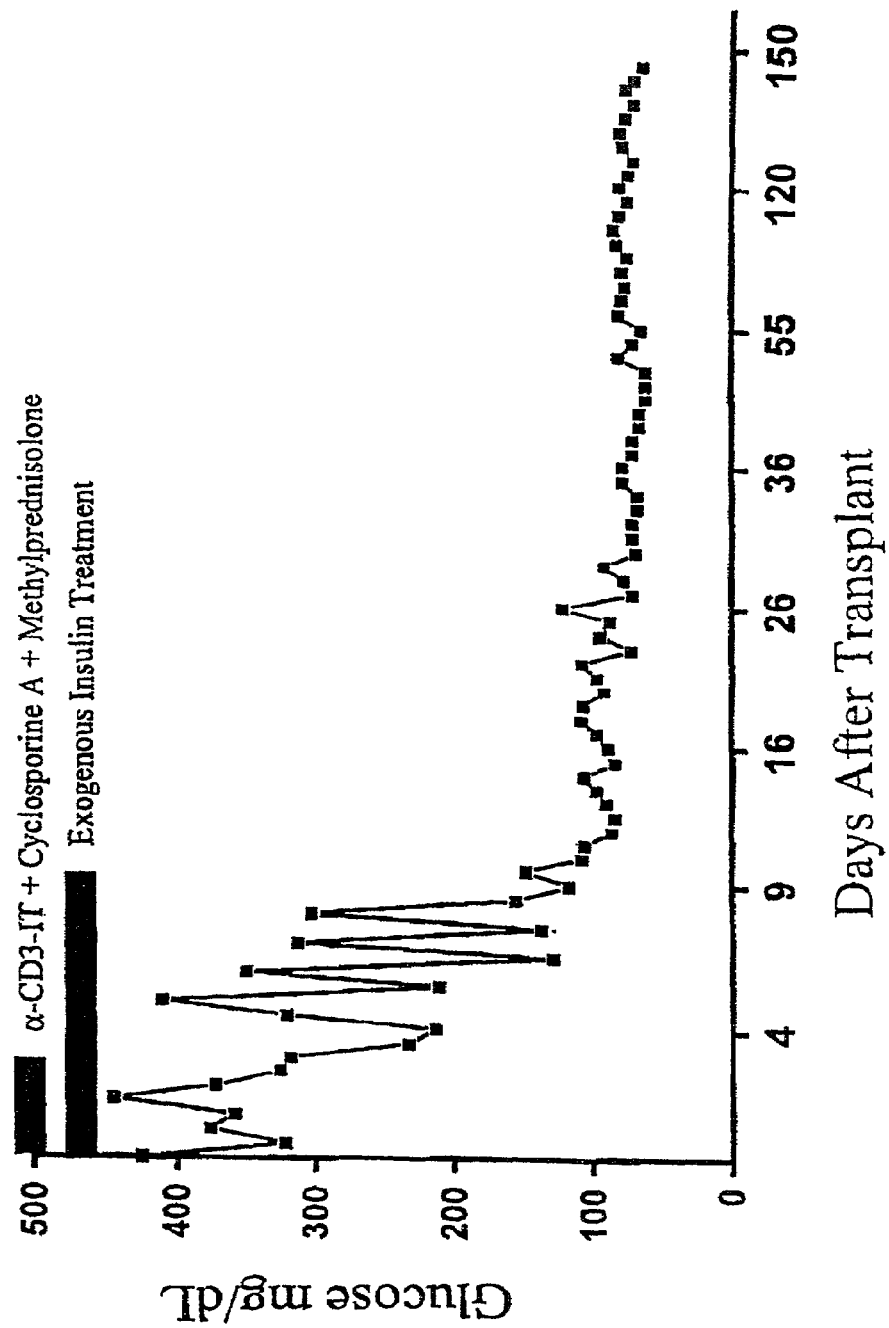
FIG. 2a shows non-fasting blood glucose values of diabetic monkey 003B from pre-islet transplant to post transplant. Day 0 is the day of transplant. Top bar indicates the duration of immunosuppression. Bottom bar indicates the duration of exogenous insulin.
Figure 2B:
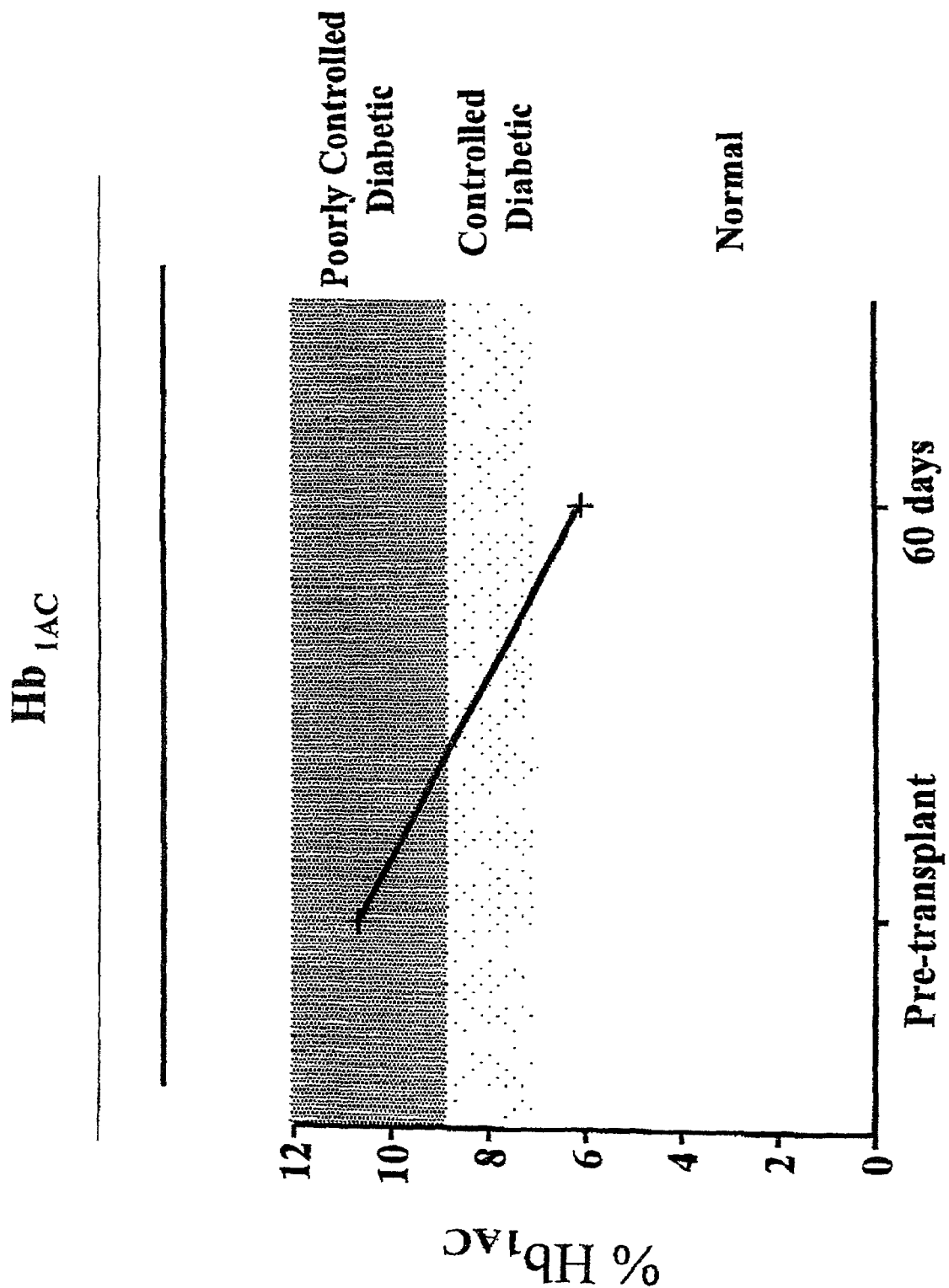
FIG. 2b shows the glycosylated hemoglobin 1AC values on diabetic monkey 003B pre islet and post islet transplant. Normal and pathological ranges are for humans.
Figure 3A:
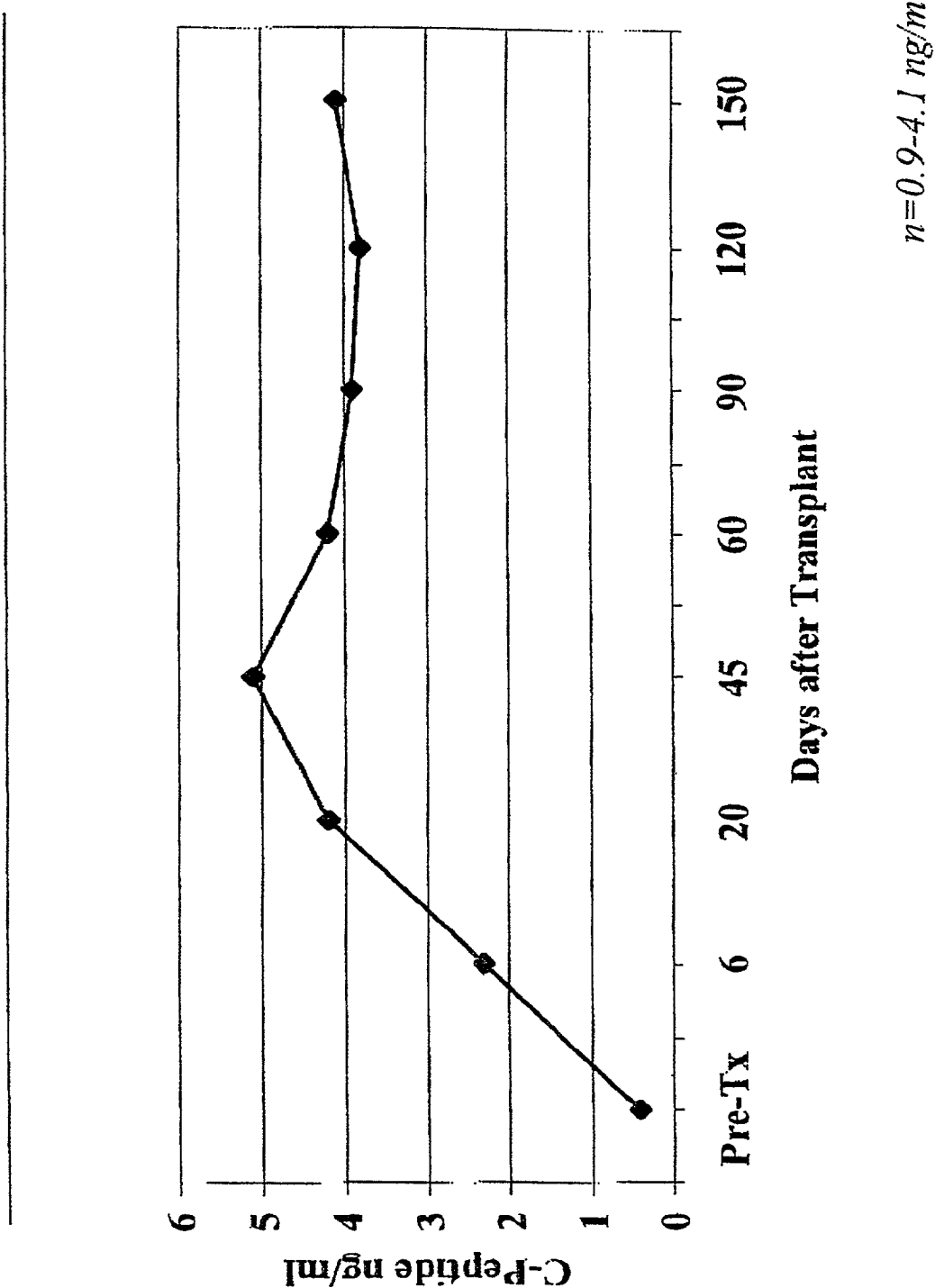
FIG. 3a shows C-peptide values for diabetic monkey 003B pre islet and post islet transplant. Normal ranges (n) are for humans.
Figure 3B:
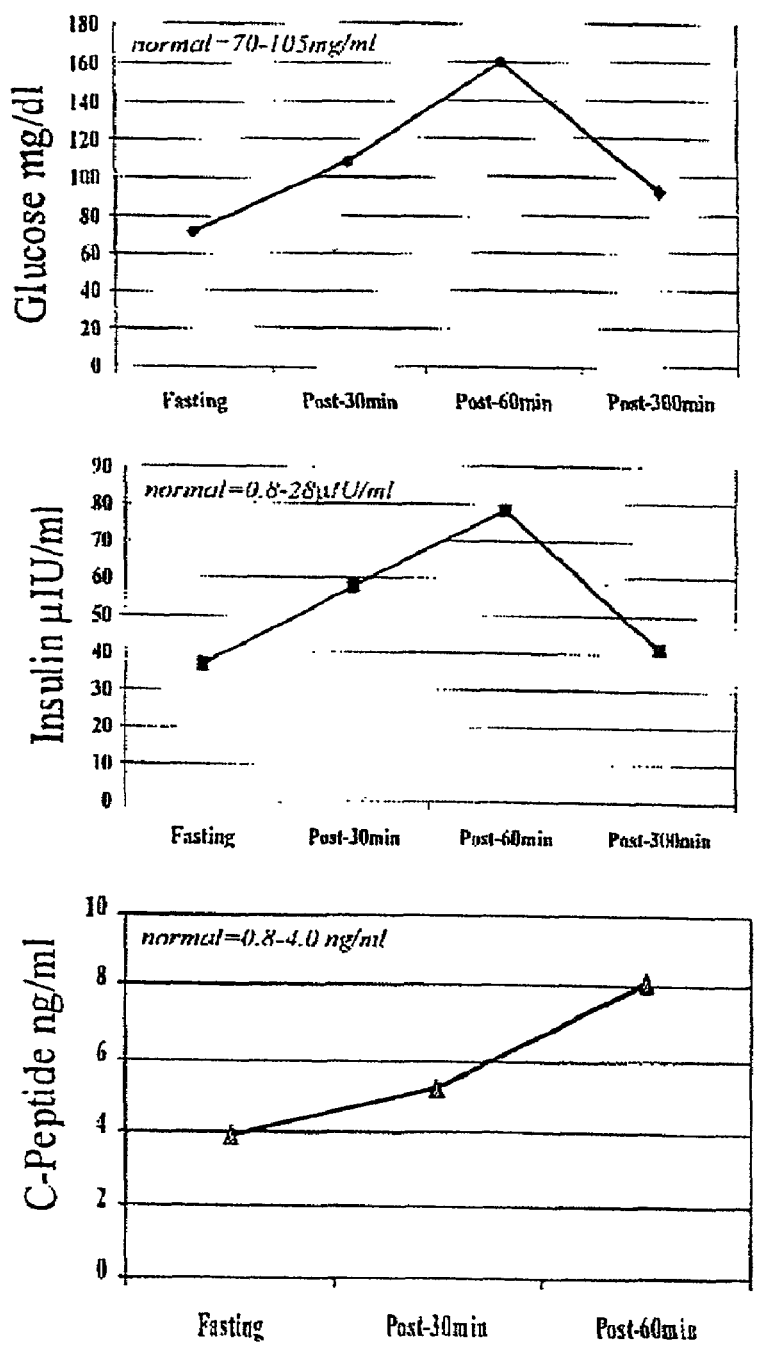
FIG. 3b shows the results of an oral glucose tolerance test performed on monkey 003B 21 days post islet cell transplant. Normal ranges are for humans. Severe hyperglycemia before transplant precluded performing this test at that time.

Caloric intake increased following transplant as did general activity. Non-fasting blood glucose values began to fall by day 4, and the monkey was off exogenous insulin by day 11. From day 12 and out to day 150 (the current duration of follow up) the monkey is normoglycemic with a mean blood glucose of 90 mgm % (FIG. 2a). Glycosylated Hemoglobin has fallen into the normal range (FIG. 2b). And C-peptide levels, indicative of islet cell insulin secretion, have risen from a subnormal level into a normal range (FIG. 3a). a post transplant glucose tolerance test is near normal and may be normal for an elderly primate (FIG. 3b).

Figure 4A:
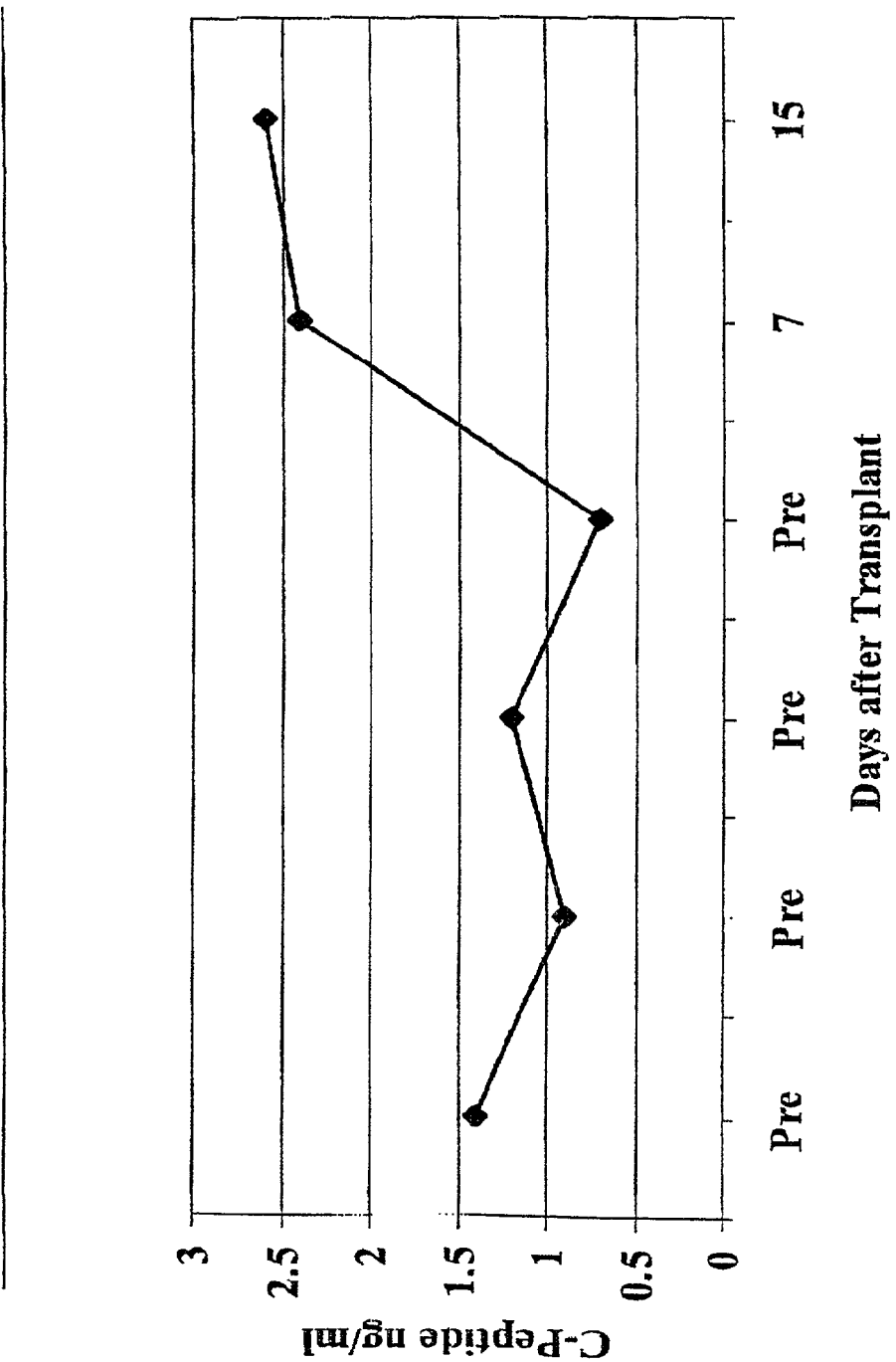
FIG. 4a shows C-peptide values for diabetic monkey X-550 pre islet and post islet transplant. Normal ranges (n) are for humans.

Monkey X550 is a long-term diabetic cynomolgous monkey who received 6 units of a mixture of human NPH and regular insulins twice daily, yet was severely hyperglycemic with blood sugars above 300 mgm % and showed elevated glycosylated hemoglobin values. This monkey was in the low normal range of C-peptide values prior to transplant (FIG. 4a) indicating insulin secretion but likely at the low end of the normal range. However, severe peripheral insulin resistance appears to be present based on the high blood sugars obtained prior to islet cell transplant in the face of both endogenous and exogenous insulin (see FIG. 4b).

Figure 4B:
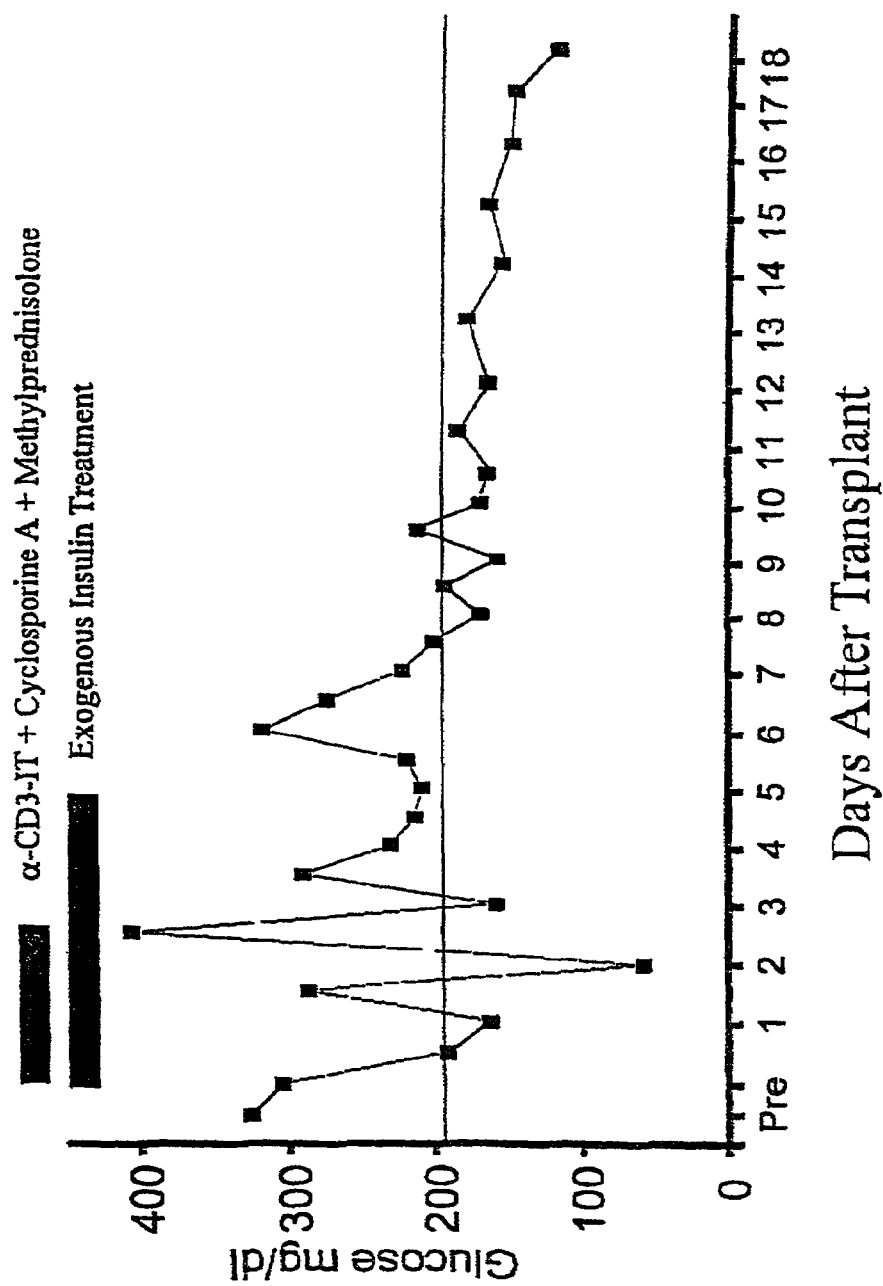
FIG. 4b shows non-fasting blood glucose values on diabetic monkey X-550 from pre-islet transplant to post transplant. Day 0 is the day of transplant. Top bar indicates the duration of immunosuppression. Bottom bar indicates the duration of exogenous insulin.

Monkey X550 received an islet cell transplant from a rhesus donor using the method described above and the same immune tolerance inducing regimen. Blood glucose declined into the normal range post transplant (FIG. 4b). Exogenous insulin was discontinued on day 5, and non-fasting blood glucose values have remained below 170 mgm % from day 12 to day 18 which is currently the last day of follow up. Post transplant C-peptide values have climbed from the low normal range into the mid normal range. The severe insulin resistance noted pre transplant seems to have been largely moderated by the presence of new islets. This would imply that in this case of insulin resistant diabetes, (1) the original islets were playing a role in the insulin resistant state and (2) the insulin resistant state could be attenuated by new healthy islets even in the presence of the faulty islets.

It should be emphasized that these stable transplants cross species lines and are, therefore, classified as congeneic or xenogeneic transplants. Thus, this immune tolerance inducing regime should also be useful in more disparate islet cell transplantation combinations crossing families and orders such as pig or fish into human.

It should be emphasized that the anti-CD3∈ immunotoxin used here can be modified and constructed by genetic engineering provided that the essential features are maintained. These are:

1. The antibody moiety must be directed at CD3∈ and the antibody moiety must be divalent and maintain an affinity of greater than $10^8$ $M^{-1}$.

2. The protein toxin moiety must be efficiently translocated by the CD3∈ receptor or the CD3∈ routing pathway.

Added benefits will accrue if the antibody moiety lacks binding to the macrophage a B cell high and low affinity receptors which permit morbidity through cytokine release syndrome.

Throughout this application various publications are referenced by numbers within parentheses. Full citations for these publications are provided below. Also, some publications mentioned hereinabove are hereby incorporated in their entirety by reference. The disclosures of these publications in their entireties are hereby incorporated by reference into this application in order to more fully describe the state of the art to which this invention pertains.

While the foregoing invention has been described in some detail for purposes of clarity and understanding, it will be appreciated by one skilled in the art from a reading of this disclosure that various changes in form and detail can be made without departing from the true scope of the invention and appended claims.

REFERENCES

1. Nicholls, P. J., Johnson, V. G., Andrew, S. M., Hoogenboom, H. R., Raus, J.
   C. and Youle, R. J. (1993) *J. Biol Chem* 268, 5302–5308.
2. Neville, D. J. (1987) Ann N Y Acad Sci 507, 155–1643.
3. Williams, D. P., Parker, K., Bacha, P., Bishai, W., Borowski, M.,Genbauffe, F., Strom T. B. and Murphy, J. R (1987) Protein Eng 1,493–498
4. Johnson, V. G. and Youle, R J. (1989) J Biol Chem 264, 17739–17744
5. Kreitman, R. J., Chaudhary, V. K., Waldmann, T. a., Hanchard, B., Cranston, B., FitzGerald, D. J. and Pastan, I. (1993) Leukemia 7, 553–562
6. Murphy, J. R. (1988) Cancer Treat Res 37, 123–124
7. Laske, D. W., Ilercil, O., Akbasak, a., Youle, R. J. and Oldfield, E. H. (1994) J Neurosurg 80, 520–526
8. Neville, D. J., Scharff, J. and Srinivasachar, K. (1992) J of Controlled Release 24, 133–141
9. Neville, D. J., Scharff, J. and Srinivasachar, K. (1992) Proc Natl Acad Sci U S a 89, 2585–2589
10. Giannini, G., Rappuoli, R. and Ratti, G. (1984) Nucleic Acids Res 12, 4063–4069
11. Chang, T. M. and Neville, D. M. J. (1977) J Biol Chem 252, 1505–1514

12. Neville, D. J., Srinivasachar, K., Stone, R. and Scharff, J. (1989) J Biol Chem 264, 14653–14661
13. Shalaby, M. R., Shepard, H. M., Presta, L., Rodrigues, M. L., Beberley, P. C. L., Feldman, M. and Carter, P. (1992) J Exp Med 175, 217–225
14. Johnson, S. and Bird, R. E. (1991) in Methods in Enzymol, pp.88–98, Academic Press, Inc., San Diego, Calif.
15. Grimont, F. and Grimont, P. A. D. (1991) in Nucleic acid techniques in bacterial systematics, pp. 252, E. A. G. Stackebrandt M. John Wiley and Sons, LTD, West Sussex, England
16. Esworthy, R S. and Neville, D. M. J. (1984) J Biol Chem 258, 11496–11504
17. Pelchen-Matthews, A., Armes, J. E., Griffiths, G. and Marsh, M. (1991) J Exp Med 173, 575–578
18. Choe, S., Bennett, M. J., Fujii, G., Curmi, P. M., Kantardjieff, K. A., Collier, R. J. and Eisenberg, D. (1992) Nature 357, 216–222
19. LeMaistre, C. F., Meneghetti, C., Rosenblum, M., Reuben, J., Parker, K., Shaw, J., Deisseroth, A., Woodworth, T. and Parkinson, D. R. (1992) Blood 79, 2547–2554
20. Platanias, L. C., Ratain, M. J., O'Brien, S., Larson, R. A., Vardiman, J. W., Shaw, J. P., Williams, S. F., Baron, J. M., Parker, K. and Woodworth, T. G. (1994) Leuk Lymphoma 14,257–262
21. Higashi, K., Asada, H., Kurata, T., Ishikawa, K., Hayami M., Spriatna, Y., Sutarman, Y. and Yamanishi, K. (1989) J Gen Virol 70,3171–3176
22. Youle, R. J. and Neville, D. M. J. (1982) J Biol Chem 257, 1598–1601
23. Williams, D. P., Snider, C. E., Strom, T. B. and Murphy, J. R.(1990) J Biol Chem 265, 11885–11889
24. Parlevliet et al. (1992) Transplant Int; 5:234–246.
25. Cosimi et al. (1981) Transplantation;32:535–9.
26. Jaffers et al. (1986) Transplantation;41:572–8.
27. Abramowicz et al. (1989) Transplantation; 47:606–8.
28. Burns et al. (1982) J Immunol;129:1451–7.
29. Parren et al. (1991) Res Immunol; 142:749–63.
30. Waid et al. (1991) Transplant Proc; 23:1062–5.
31. Khazaeli et al. (1994) J Immunotherapy; 15:42–52.
32. Chen C and Okayama H. (1987); Mol Cell Biol 7:2745–52.
33. Slavin-Chiorini et al. (1993) Int J Cancer; 53:97–103.
34. Rigaut KD, Scharff JE, Neville DM Jr. (1995) Eur J Immunol;25:2077–82.
35. Woodle E S, Thistlethwaite J R, Jolliffe L K, et al. (1992) J Immunol; 148:2756–63.
36. Miller A D, Rosman G J. (1989) BioTechniques 7:980–90.
37. Shu L M, Qi C F, Schlom J, Kashmiri S V S (1993) Proc Natl Acad Sci USA;90:7995–9.
38. Mosmann T R, Williamson A R (1980) Cell; 20:283–92.
39. Capon D J, Chamow S M, Mordenti J, et al. (1989) Nature 337:525–31.
40. Anand N N, Mandal S, MacKenzie C R, et al. (1991) J Bio Chem 266:21874–9.
41. Sitia R, Neuberger M, Alberini C M, et al. (1990) Cell;60:781–90.
42. Alberini C M, Bet P, Milstein C, Sitia R. (1990) Nature 347:485–7.
43. Fra A M, Fragioli C, Finazzi D, Sitia R, Alberini C M (1993) The EMBO Journal; 12:4755–61.
44. Wiersma E J, Shulman M J (1995); 154:5265–72.
45. Smith K G, Austyn J M, Hariri G, Beverley P C, Morris P J (1986) Eur J Immunol; 16:478–86.
46. Tax W J, Hernes F F, Willems R W, Capel P J, Koene R A (1984) J Immunol;133:1185–9.
47. Lynch, R G, Sandor M., Metzger H, ed. Washington DC: American Society for Microbiology 1990:305–34.
48. Moretta I, Webb S R, Grossi C E, Lydyard M, Cooper M D. (1977) J Exp Med;146:184–200.
49. Ferrarini M, Moretta L, Mingari M C, Tonda P, Pernis B. (1976) Eur J Immunol;6:520–1.
50. Mathur a, Lynch RG, Kohler G (1988);J Immunol; 140:143–7.
51. Pricop L, Rabinowich H, Morel P A, Sulica a, Whiteside T L, Herberman R B (1993) J Immunol; 151:3018–29.
52. Emara M, Sanfilippo F (1992) Cell Immunol; 144: 143–54.
53. Glu M, Gordon V M, Fitzgerald D J, Leppla S (1996) Infect. and Immun.; 64(2):524–527.
54. Kuan C T, Pastan I (1996) Proc. Natl. Acad. Sci. USA; 93:974–978, 1996.
55. Francisco J A, Kiener P A, Moran-Davis P, Ledbetter J A, Siegall C B (1996) J. Immunol.; 157:1652–1658.
56. Kaczorek M, Delpeyroux F, Chenciner N, Streeck R (1983) Science; 221:855
57. Shen W H, Choe S, Eisenberg D, Collier R J (1994). Biol. Chem.; 469(46):29077–29084.
58. Muhlrad D, Hunter R, Parker R (1992) Yeast; 8:79–82.
59. Madshus I H, Stenmark E, Snadvig K, Olsnes S (1991) J. Biol. Chem.; 266(26): 17446–53.
60. Federal Register, Notices, May 7, 1986), Appendix F-II-B, p. 16971.
61. Perkins S J, Nealis A S, Sutton B J, Feinstein a (1991) J. Mol. Biol., 221:1345–1366.
62. Theuer, C P, Kreitman R J, FitzGerald D J, Pastan I (1993) Cancer Res., 53:340–347.
63. Kihara a, Pastan 1 (1994) Cancer Res., 54:5154–5159.
64. Chaudry G J, Fulton R J, Draper R K (1993) J. Biol. Chem., 268(13):9437–9441.
65. Schmidt M, Hynes N E, Groner B, Wels W (1996) Int. J. Cancer, 65:538–546.
66. Better M, Bernhard SL, Lei S P, Fishwild D M, Lane J A, Carroll S F, Horwitz A H (1993) Proc. Natl. Acad. Sci USA, 90:457461.
67. Thompson J, Hu H, Scharff J, Neville, Jr. D (1995) J. Biol. Chem., 24:28037–28041.
68. Ma S, Thompson J, Hu Neville, Jr. D (1996) Scand. J. Immunol. 43:134–139.
69. Neville, Jr. D, Scharff J, Hu H, Rigaut K, Shiloach J, Singerland W, Jonker M (1996) J. Immunotherapy 19(2): 85–92.
70. Knechtle S, Vargo D, Fechner J, Zhai Y, Wang J, Hanaway M, Scharff J, Hu H, Knapp L, Watkins D, Neville, Jr. D (1997) Transplantation 63(6):1–6.
71. Cellular and Molecular Approaches to Achieving Euglycemia (1997), NIH Guide 26(38).
72. Krowlewski A S, Laffel L M B, Krolewski M, Quinn M, Warram J H (1995) N. Engl. J. Med. 332:1251–55.
73. Alejandro R, Lehmann R, Ricordi C, Kenyon S, Angelico M C, Burke G, Esquenazi V, Nery J, Betancourt A E, Kong S S, Miller J, Mintz D H (1997) Diabetes 46:1983–89.
74. Henretta J, McFadden T., Pittman K, Thomas J, Thomsa F (1994) Transplantation Proceedings 26: 1138–39.
75. Rilo H L R, Carroll P B, Shapiro R, Jordan M, Scantlebury V, Rastellini C, Fontas P, Alejandro R, Mintz D H, Fung J J, Ricordi C, Starzl T E, Rao A S (1995) Transplantation Proceedings27:3162–63.

What is claimed:

1. A method of transplanting cadaveric donor pancreatic islet cells to a subject in need thereof, comprising
    (a) administering to the subject a divalent anti-T cell diphtheria toxin binding site mutant immunotoxin directed at the CD3 epitope during the peritransplant period, thereby reducing the subject's T-cell population;
    (b) administering deoxyspergualin to the subject; and
    (c) administering to the subject pancreatic islet cells from a cadaveric donor.

2. The method of claim 1, wherein the immunotoxin transiently reduces the subject's T cells in the blood and lymph nodes by at least one log unit.

3. The method of claim 1, wherein the anti-T cell immunotoxin is UCHT1-CRM9.

4. The method of claim 1, wherein the deoxyspergualin is administered beginning 0 to 24 hours prior to administration of the pancreatic islet cells to the recipient and continuing up to several weeks thereafter.

5. The method of claim 1, wherein the immunotoxin is administered beginning at up to several hours before administration of the pancreatic islet cells and continuing up to several days thereafter.

6. A method of inhibiting a rejection response of a recipient of a cadaveric donor pancreatic islet transplant by inducing immune tolerance in the recipient, comprising administering a divalent anti-T cell diphtheria toxin binding site mutant immunotoxin directed at the CD3 epitope and deoxyspergualin during the peritransplant period, thereby transiently reducing the number of T-cell lymphocytes and promoting long-term survival of the transplant.

7. The method of claim 6 further comprising administering mycophenolate moefitil to the subject.

8. The method of claim 1 further comprising administering mycophenolate moefitil to the subject.

* * * * *